(12) United States Patent
Iyer et al.

(10) Patent No.: US 9,040,234 B2
(45) Date of Patent: May 26, 2015

(54) OLIGONUCLEOTIDE ANALOGS AS THERAPEUTIC AGENTS

(75) Inventors: Radhakrishnan P. Iyer, Shrewsbury, MA (US); John E. Coughlin, Auburn, MA (US)

(73) Assignee: SPRING BANK PHARMACEUTICALS, INC., Milford, MA (US)

( * ) Notice: Subject to any disclaimer, the term of this patent is extended or adjusted under 35 U.S.C. 154(b) by 492 days.

(21) Appl. No.: 13/218,259

(22) Filed: Aug. 25, 2011

(65) Prior Publication Data

US 2012/0053226 A1 Mar. 1, 2012

Related U.S. Application Data

(60) Provisional application No. 61/402,380, filed on Aug. 30, 2010.

(51) Int. Cl.
| | | |
|---|---|---|
| A61K 31/713 | (2006.01) | |
| A61K 31/7084 | (2006.01) | |
| A61P 31/00 | (2006.01) | |
| A61P 31/12 | (2006.01) | |
| C07H 21/04 | (2006.01) | |
| C12Q 1/68 | (2006.01) | |
| C12Q 1/70 | (2006.01) | |
| C25B 7/00 | (2006.01) | |
| G01N 27/447 | (2006.01) | |
| G01N 33/559 | (2006.01) | |

(52) U.S. Cl.
CPC ............ *C07H 21/04* (2013.01); *A61K 31/7084* (2013.01); *A61K 31/713* (2013.01)

(58) Field of Classification Search
CPC ... A61K 31/7084; A61K 31/713; C07H 21/04
See application file for complete search history.

(56) References Cited

U.S. PATENT DOCUMENTS

| | | | |
|---|---|---|---|
| 8,076,303 B2 * | 12/2011 | Iyer et al. | 514/43 |
| 8,404,651 B2 * | 3/2013 | Iyer et al. | 514/43 |
| 8,691,787 B2 * | 4/2014 | Iyer et al. | 514/48 |
| 2005/0256073 A1 | 11/2005 | Lipford et al. | |
| 2006/0130161 A1 | 6/2006 | Genain | |
| 2010/0040576 A1 | 2/2010 | Kao et al. | |

FOREIGN PATENT DOCUMENTS

| | | |
|---|---|---|
| WO | 02/092006 A2 | 11/2002 |
| WO | 2005/060377 A2 | 7/2005 |
| WO | 2007/070598 A2 | 6/2007 |
| WO | 2008/017473 A2 | 2/2008 |
| WO | 2009/146123 A2 | 12/2009 |

OTHER PUBLICATIONS

International Search Report dated Apr. 10, 2012 for corresponding PCT Appln. No. PCT/US2011/049213.
Supplementary European Search Report dated Dec. 12, 2013 for copending EP Appln. No. EP 11 822 383.3.
European Search Opinion dated Dec. 18, 2013 for copending EP Appln. No. EP 11 822 383.3.
Abramova et al., "A facile and effective synthesis of dinucleotide 51-triphosphates", Bioorganic & Medicinal Chemistry, Pergamon, GB, vol. 15, No. 20, pp. 6549-6555 (2007).
Padmanabhan S. et al., "Anti-HBV nucleotide prodrug analogs: Synthesis, bioreversibility, and cytotoxicity studies", Bioorganic & Medicinal Chemistry Letters, Pergamon, GB, vol. 16, No. 6, pp. 1491-1494 (2006).

* cited by examiner

*Primary Examiner* — Lawrence E Crane
(74) *Attorney, Agent, or Firm* — Lando & Anastasi LLP

(57) ABSTRACT

The invention relates to design of short oligonucleotides and analogs thereof (such as, di-, and trinucleotide compounds) useful for various therapeutic applications. It is believed that the compounds of the invention can be used as antiviral agents, anticancer agents and so on. In certain embodiments, the compounds of the invention can modulate immune-stimulatory pathways and non-TLR pathways. The invention also relates to design modified oligonucleotides for therapeutic applications, by excluding nucleotide segments having off-target effects from the modified oligonucleotides. In another aspect, the invention provides pharmaceutical compositions including one or more compounds of the invention.

It is believed that the compounds and compositions as described herein have therapeutic utility against a variety of diseases, including viral diseases, autoimmune diseases (such as, allergy, asthma, and inflammatory disorders) and cancer.

1 Claim, 8 Drawing Sheets

6k Has Demonstrated Synergy with Several Drug Combinations in Vitro[1]

| Drug | EC$_{50}$ (uM) | Ratio | EC$_{50}$Comb (uM) | Comments |
|---|---|---|---|---|
| 6k | 1.5- 2.3 | | | |
| +Interferon α | 2.1 | 3:1 | 0.662 | Synergistic |
| | | 1:1 | 0.643 | Synergistic |
| | | 1:3 | 0.656 | Synergistic |
| +Ribavirin | >30 | 1:30 | 2.3 | Synergistic |
| +Ribavirin + Interferon α | | 3:1 | 0.777 | Synergistic |
| | | 1:1 | 0.629 | Synergistic |
| | | 1:3 | 0.686 | Synergistic |
| + 2C$_u$Cyt (NM 283) | 1.4 | 3:1 | 0.522 | Synergistic |
| | | 1:1 | 0.494 | Synergistic |
| | | 1:3 | 0.462 | Additive |
| +Vertex (telaprevir) | 0.250 (CC$_{50}$<80) | 100:1 | 0.108 | Synergistic |
| | | 30:1 | 0.126 | Synergistic |
| | | 10:1 | 0.118 | Synergistic |

FIG. 9

OLIGONUCLEOTIDE ANALOGS AS THERAPEUTIC AGENTS

RELATED APPLICATIONS

This application claims the benefit of U.S. provisional application No. 61/402,380, filed on Aug. 30, 2010. The entire teachings of the afore-mentioned application are incorporated herein by reference.

BACKGROUND OF THE INVENTION

Innate immunity plays a critical role in the body's defense against prokaryotic and eukaryotic pathogens such as viruses, bacteria, fungii, parasites etc. Indeed, acute and chronic infections caused by viruses constitute a major worldwide public health crisis with significant unmet medical need. In addition to infectious diseases, viruses cause 15-20% of all cancers worldwide including liver, cervical, and pancreatic cancers, each resulting in significant mortalities and morbidities. In addition to human suffering, viral diseases result in overwhelming healthcare costs and loss of productivity. For example, worldwide 500 to 600 million people are chronically infected with HBV and HCV, and 1 to 2 million deaths occurs every year due to virus-induced liver cirrhosis and liver cancer. Tens of thousands of patients worldwide are in desperate need of liver transplantation. Human papilloma virus infection leads to cervical cancer and incidence of Kaposi sarcoma associated with HIV infection is all well documented. Pandemic influenza is characterized by high levels of morbidity and mortality in humans, and associated with increased levels of infection and pathogenesis due to the lack of pre-existing immunities against its novel antigenic subtype. Antivirals may not only potentially slow the spread of pandemic influenza, but may ultimately be a solution.

Although vaccines are available as prophylactic against a limited number of viruses, they have no real therapeutic benefit for those already infected. Moreover, vaccines against certain viruses (e.g., influenza vaccines) are unlikely to make a significant impact on mortality in a pandemic because of the time required to generate enough doses of a suitable vaccine against the new human strain after it has been identified.

Consequently, our antiviral defense almost exclusively relies on the use of antiviral drugs. Unfortunately, many medically important viruses, particularly RNA viruses are dangerous, cannot be tested in model systems, or cannot be propagated for testing of potential candidate drugs. Further, it has been noted that viruses have also continuously evolved clever strategies to evade host immune response and to develop resistance to drugs through a variety of mechanisms.

Many of the current antiviral drugs have been developed as viral polymerase, protease, integrase, and entry inhibitors. However, drugs designed to inhibit viral growth can also adversely affect host cells since viral life cycle engages normal host cellular functions. The limited viral targets that are amenable to antiviral intervention further compound antiviral drug discovery. Consequently, despite almost 50 years of antiviral research, the arsenal of antiviral drugs remains dangerously small with only about 34 antiviral drugs in the world market, mostly against HIV and Herpes viruses. In addition, the current treatment options for several chronic viral diseases including HCV and HBV remain extremely limited and challenging. Indeed, viral rebound upon cessation of therapy, drug-induced toxicity, and emergence of resistant strains under selective pressure of antiviral drugs continue to remain serious problems in current antiviral therapy. Complete eradication of the virus is rarely achieved, and at best in a very small cohort of patients, because current antiviral therapy produces inadequate and unsustainable antiviral response.

There is indeed a need for the development of new drugs with an alternate strategy for antimicrobial discovery.

SUMMARY OF INVENTION

The present inventors have discovered that certain short oligonucleotide compounds have the potential to stimulate innate immune response and cause activation of IRF3, produce cellular interferons and induce the production of antimicrobial peptides. In one embodiment, the compounds of the invention are di-, and trinucleotide compounds having the capability of stimulating innate immune responses. In certain embodiments, the short oligonucleotide compounds of the invention contain at least one chemical modification.

It is believed that the compounds of the invention have antimicrobial activities, and thus can be used as antimicrobial agents. In one embodiment, the compounds have broad-spectrum antiviral activities against multiple viral genotypes and resistant strains.

In certain instances, the compounds of the invention have inhibitory activities against a RNA and/or DNA viruses. Such RNA and/or DNA viruses can be, for example, hepatitis viruses (e.g., HCV and HBV etc.), human papillomavirus (HPV), Sendai, Vaccinia, influenza and other flaviviruses.

The compounds of the invention, or their pharmaceutically acceptable salts or pharmaceutically acceptable formulations are useful in the prevention and treatment of viral infections and other conditions caused by hepatitis viruses, such as, liver inflammation, liver cirrhosis, acute hepatitis, fulminant hepatitis, chronic hepatitis, and other liver diseases. The compounds and formulations of the invention can also be used prophylactically to prevent disease progression in hepatitis-infected individuals.

One embodiment provides that the compound of the invention has immunostimulatory properties. Another embodiment provides that the compound is useful as an anticancer agent.

In another embodiment, it is believed that the compounds are synergistic with other antivirals for use in a combination therapy. In another embodiment, the compound of the invention has broad-spectrum antibacterial and antiparasitic activity.

In one aspect, the invention relates to a compound of formula (I):

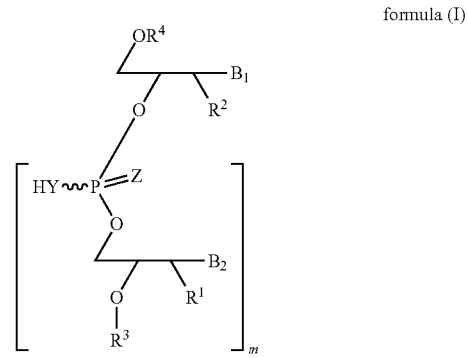

formula (I)

or pharmaceutically acceptable salts, racemates, enantiomers, diastereomers, geometric isomers, or tautomers thereof,
wherein
$R^1$ and $R^2$, each independently, are H, OH, —O-akyl, alkyl, substituted alkyl, cycloalkyl, aryl, substituted aryl, aralkyl, heterocyclyl, —O-aryl, or O-heteroarylaryl;

R³ is selected from hydrogen, alkyl, substituted alkyl, —C(O)-alkyl, —C(O)O-alkyl, —C(O)-aryl, —C(O)O-aryl, —C(O)NH-alkyl, and —C(O)NH-aryl;
Y and Z, each independently, are O or S;
B₁ and B₂, on each occurrence, independently are adeninyl, guaninyl, thyminyl, cytosinyl, uracil, or a modified nucleoside moeity;
m=1, 2, 3, 4, 5, or 6;
R⁴, on each occurrence, independently is a monophosphate, diphosphate, or triphosphate group.

In one embodiment, the compound of formula (I) is not Compound 5 (see infra.).

In one embodiment, the compound of formula (I) has antimicrobial activity and is capable of inducing cellular production of peptides in vitro or in vivo.
In particular, the compound is

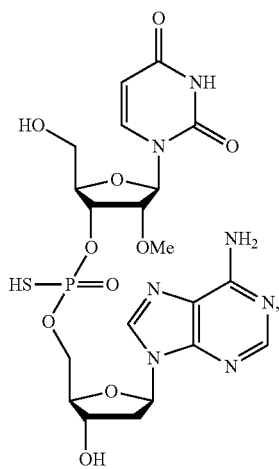
(Compound 5)

or pharmaceutically acceptable salts, racemates, enantiomers, diastereomers, geometric isomers, or tautomers thereof.

In another aspect, the invention provides a compound of formula (II):

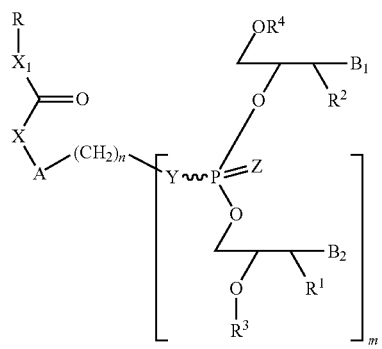
formula (II)

or pharmaceutically acceptable salts, racemates, enantiomers, diastereomers, geometric isomers, or tautomers thereof,
wherein
X=absent, O, NH, NR, or S;
X₁=absent, O, or NH;
A=absent, aryl, or aralkyl;
n=0, 1, 2, 3, 4, or 5;
R=alkyl, substituted alkyl, cycloalkyl, aryl, substituted aryl, aralkyl, heterocylyl, —O-alkyl, —O-heteroaryl, or steroidal;
R¹ and R², each independently, are H, OH, —O-akyl, alkyl, substituted alkyl, cycloalkyl, aryl, substituted aryl, aralkyl, heterocyclyl, —O-aryl, or —O-heteroarylaryl;
R³ is selected from hydrogen, alkyl, substituted alkyl, —C(O)-alkyl, —C(O)O-alkyl, —C(O)-aryl, —C(O)O-aryl, —C(O)NH-alkyl, and —C(O)NH-aryl;
Y and Z, each independently, are O or S;
B₁ and B₂, on each occurrence, independently are adeninyl, guaninyl, thyminyl, cytosinyl, uracil or a modified nucleoside moeity;
m is 1, 2, 3, 4, 5, or 6;
R⁴, on each occurrence, independently is a monophosphate, diphosphate, or triphosphate group.

In one embodiment, the compound of formula (II) is not Compound 6k (see infra.). In another embodiment, R⁴ is not H when m is 2.

In one embodiment, the compound is capable of inducing cellular production of antimicrobial peptides. In one instance, the compound is

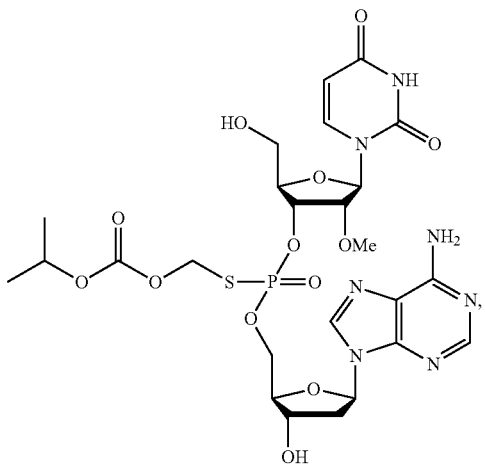
(Compound 6k)

or pharmaceutically acceptable salts, racemates, enantiomers, diastereomers, geometric isomers, or tautomers thereof.

This invention also relates to the use of certain cellular peptides as biomarkers for predicting effectiveness of antimicrobial activity of drugs. For example, in hepatitis C and hepatitis B patients, the presence of the biomarker can be used to predict effectiveness of antiviral therapy, for example, viral reduction and sustained viral response following administration of interferon.

One embodiment provides a method of measuring an antimicrobial response in a subject suffering from an antimicrobial infection using cellular EEEH protein as a biomarker.

Further, the invention relates to a method of modulating immune-mediated effects of a double-stranded RNA in a subject. In one embodiment, the method comprises administering to the subject an effective amount of siRNA having a nucleotide segment(s) of a compound of the invention. In another embodiment, the method comprises administering to the subject an effective amount of siRNA having dinucleotide overhangs of a compound of the invention.

A method of modulating immune-mediated effects of a single-stranded RNA in a subject is also provided. The method comprises administering to the subject an effective amount of a chemically modified RNA having a nucleotide segment(s) of a compound of the invention.

In another embodiment, the invention provides a method of modulating immune-mediated effects of a single-stranded RNA in a subject, by administering to the subject an effective amount of a chemically modified RNA having a nucleotide segment(s) of a compound of the invention.

The invention also provides a method of modulating immune-mediated effects of a single-stranded RNA having a chemically modified nucleotide segment(s). In one embodiment, a dinucleotide having ends chemically modified (such as, dA-ps-U2'OMe) is used.

In one aspect, the invention relates to a method of minimizing off-target effects of a synthetic oligonucleotide. The method comprises a) identifying chemical modifications on an oligonucleotide, wherein said chemical modifications will cause a modified oligonucleotide having undesirable immune-mediated effects; and b) excluding said chemical modifications when designing the synthetic oligonucleotide for therapeutic applications.

One aspect of the invention provides a method of enhancing anticancer effects of chemically modified oligonucleotides in a subject. The method comprises administering to the subject an effective amount of a compound of the invention, which is capable of stimulating apoptotic pathways.

Also, the invention provides a method of minimizing off-target effects of a chemically modified oligonucleotide, which comprises excluding from use a segment of a compound of the invention, when the segment is identified to have caused undesirable immune-mediated effects.

In one embodiment, the invention relates to a method of designing a modified oligonucleotide for therapeutic applications. The method comprises a) providing a nucleotide segment(s) of a compound, wherein said compound is

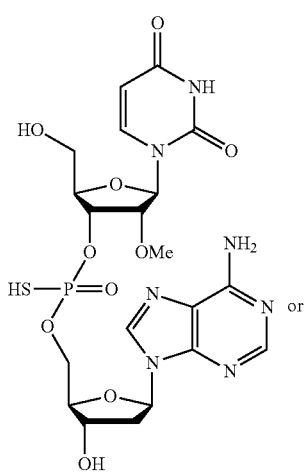

or

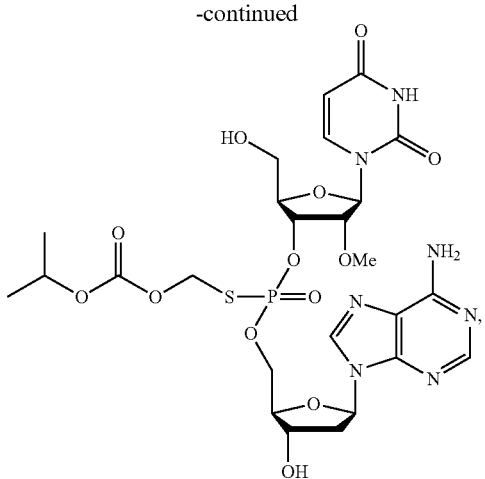

or an analog thereof;

b) evaluating off-target effects of said nucleotide segment; and c) excluding said nucleotide segment from the modified oligonucleotide.

The invention further provides a method of treating a viral infection or a cancer in a subject through administering to the subject any effective amount of a compound of the invention.

In another aspect, the invention relates to pharmaceutical compositions for use to inhibit microbial activities, with the pharmaceutical compositions containing an effective amount of a compound of the invention.

A method for the treatment of a viral infection in a host, including human, is also disclosed that includes administering an effective amount compound of the invention including a pharmaceutically active salt thereof, administered alone or in combination or sequentially with another or other antiviral agent(s).

A method for the treatment of a bacterial infection in a host, including human, is also disclosed that includes administering an effective amount compound of the invention, administered alone or in combination or sequentially with another or other agent(s).

A method for the treatment of a parasitic infection in a host, including human, is also disclosed that includes administering an effective amount compound of the invention, administered alone or in combination or sequentially with another or other agent(s).

A method for the treatment of a fungal infection in a host, including human, is also disclosed that includes administering an effective amount compound of the invention, administered alone or in combination or sequentially with another or other agent(s).

The compounds of the invention include di-, and tri-nucleotides. Certain examples of the di-, and tri-nucleotides include, but are not limited to, 3-dApsU$_{2'\text{-}OMe}$, 3'dApsA$_{7deaza}$, and 3'-dApsTpsC and their analogs where "ps" refers to phosphorothioate internucleotidic linkages.

The compounds described herein can be administered by multiple delivery routes such as oral, intravenous, sublingual, intranasal, topical and so on Since many interferon-associated gene products are capable of inducing apoptosis, the compounds may induce selective cell death of microbe-infected (e.g., virus-infected) cells. Similarly, induction of the cellular antimicrobial peptides may also induce selective apoptosis of cancer cells.

Hence, the compounds and compositions described herein may be used either alone or in combination with other compounds as anticancer agents.

The invention also teaches one skilled in the art the choice of nucleotide compositions for the optimal design of oligonucleotides (antisense and siRNA) for improved and selective targeting of RNA and proteins and receptors (aptamers, immunomodulatrory oligonucleotides).

BRIEF DESCRIPTION OF THE DRAWINGS

The present invention is further described below with reference to the following non-limiting examples and with reference to the following figures, in which:

FIG. 9 is a table summarizing $EC_{50}$ value of Compound 6k and its activity in combination with other classes of anti-HCV drugs in replicon assays.

DETAILED DESCRIPTION OF THE INVENTION

Figure 1:
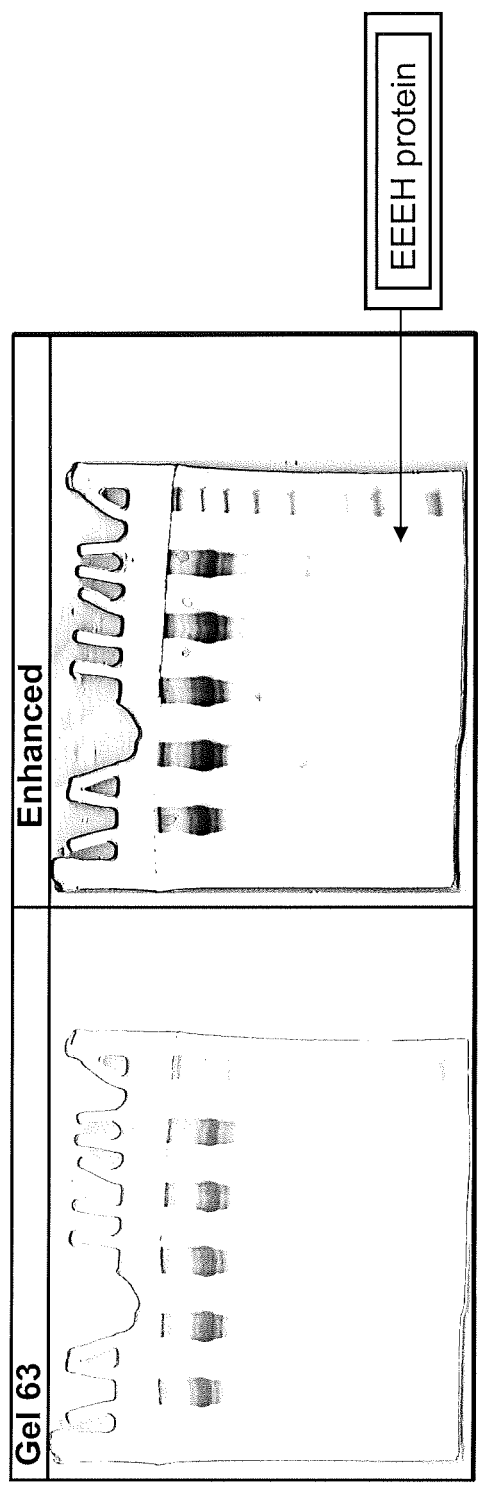
FIG. 1 shows increased expression of extra-erythrocytically derived hemoglobin (EEEH) as antiviral peptide in hepatitis B virus infected transgenic mouse treated with Compound 6k.

Viruses have also continuously evolved clever strategies to evade host immune response and to develop resistance to drugs through a variety of mechanisms. It has been recognized that both DNA and RNA viruses inhibit type I Interferon (IFN) production thereby suggesting that controlling the IFN response is essential for the survival of a broad range of viruses (Akira, S. et al. Cell, 24, 783-801, 2006; and Katze et al. Nature Reviews, 2, 675, September 2002). Thus, the development of effective antiviral therapies must involve the use of combinations of new classes of drugs each with novel, multiple mechanisms of action including those that stimulate host immune response for eradication of the virus.

Vertebrate systems are constantly under attack by invading microorganisms and have evolved immune-mediated defense for elimination of the pathogen. The mammalian immune system comprises of components of innate and acquired immunity. Innate immune system recognizes microorganisms via a limited number of germ-line encoded pathogen recognition receptors (PRRs) (Akira, S. et al. *Cell*, 24, 783-801, 2006; and Katze et al. *Nature Reviews*, 2, 675, September 2002). Phagocytes such as macrophages and dendritic cells mediate the innate immune response. Acquired immune response is characterized by specificity that involves lymphocytes that carry antigen-specific receptors generated by mechanisms such as gene-rearrangement. Innate immunity plays an important role in regulating liver injury, fibrosis, and regeneration. For example, activation of natural killer cells (NK cells) by Interferons could be a novel strategy to treat liver fibrosis. This is because activation of NK cells can kill specifically activated hepatic stellate cells (HSCs) thereby ameliorating liver fibrosis and liver tumor formation. Hence the oligonucleotide analogs disclosed in this invention may have utility in inhibiting liver fibrosis, and progression of liver cancer.

It is being increasingly recognized that virus infection of cells trigger immune-mediated antiviral response through PRRs of the host that bind to pathogen-associated molecular patterns (PAMPs) within viral products thereby resulting in activation of intracellular signaling pathways (3,4). Toll-like receptors (TLRs) are integral membrane glycoproteins characterized by the extracellular domains containing varying number of leucine-rich repeat (LRR) motifs and a cytoplasmic signaling domain homologous to interleukin 1 receptor. TLRs are evolutionarily conserved from worms to mammals (Takeda, K. et al., *International Immunology*, 17, 1-14, 2005). TLRs can recognize a wide variety of ligands such as lipopolysaccharides, the plant diterpene paclitaxel, the fusion protein of RSV, fibronectin, and heat shock proteins all having a variety of structures. TLRs 1, 2, 4, 5, and 6 are expressed on cell surfaces whereas TLRs 3, and 7-9 are expressed in intracellular compartments such as endosomes. TLRs recognize, bacteria including mycobacteria, fungi, protozoan parasites and viruses. The various viral structural components including microbial DNA, double-stranded RNA, single-stranded RNA, surface glycoproteins, cell wall components such as muramyl dipeptide are recognized as PAMPs. TLRs 3, 7, 8 and 9 are involved in the recognition of viral nucleic acids including DNA viruses. TLR 9 recognizes genomes of Herpes simplex virus 1, 2 and murine cytomegalovirus that are rich in CpG DNA motifs. It is recognized that CpG DNA activates inflammatory cytokines and type I IFN secretion by stimulation of TLR 9. Thus, the recognition of nucleic acids by PRRs commonly induces type I IFN production that can activate target cells for antimicrobial action.

Microbes have also evolved to evade immune response that protect host cells from infection. Indeed, both DNA and RNA viruses inhibit cellular IFN production (type-I, IFN-α, IFN-β). Intracellular IFNs are potent antiviral cytokines whose expression/production is mediated by the transcription factor IRF3 (IFN regulatory factor 3) present in the cytoplasm of uninfected cells. IRF3 is activated once the cells are infected and viral components (also known as pathogen associated molecular patterns (PAMPS, e.g., viral genome, viral proteins etc) are recognized by specialized viral sensors or pattern recognition receptors (PRRs). Activated IRF3 translocates to the nucleus to transactivate IFN gene expression. IFN production induces protective antiviral effects (via paracrine and autocrine activity) through a variety of mechanisms such as, (i) activation of innate and adaptive immune responses, (ii) induction of antiviral state in cells by production of antiviral and beneficial pro-inflammatory factors, and (iii) controlled apoptosis of virus-infected cells. PRRs are therefore essential components of the IFN-response. Most recently, NOD2, a member of the family of nucleotide oligomerization domain (NOD) proteins, has been found to be a PRR which detects single-stranded RNA (ssRNA) viruses including RSV and influenza A. Interestingly, like the viral sensor RIG-I, activation of NOD2 also results in triggering the signaling cascade for IFN production and the induction of NF-κβ, which promotes a controlled pro-inflammatory response to potentiate the antiviral action of IFN. Since, NOD2 is a viral sensor that detects a broad range of ssRNA viruses such as RSV and Influenza A, it presents a unique host target for antiviral discovery and to combat antiviral resistance.

Similar to NOD2, RIG-I is a host cytosolic protein that recognizes double-stranded viral RNA as a PAMP that activates type1 interferon immune defenses thereby inhibiting viral replication and also suppressing cellular permissiveness for virus infection (see, e.g., Saito, T. et al., *Proc. Natl. Acad. Sci. USA*, 10, No. 2, 582-587, 2007; Meylan, E. et al., *Nature*, 437, 1167-1172, 2005; Hiscott, J. et al. *TRENDS in Molecular Medicine*, 12, 53-56, 2006; Cui, S. et al., *Molecular Cell*, 29, 169-179, 2008; Yoneyama, M., et al., *Nat. Immunol.* 5, 730-737, 2004; Hornung, V. et al., *Science*, 314, 994-997, 2006; Pichlmair, A. et al., *Science*, 314, 997-1001, 2006; Myong, S. et al., *Science*, 323, 1070, 2009; and Gack, M. U., et al. *Proc Natl Acad Sci USA*. 105(43):16743-8, 2008). RIG-I is a viral sensor that detects a broad range of RNA viruses such as flaviviruses including Hepatitis C Virus, Sendai virus, Influenza virus, as well as, Vesicular stomatitis virus, Rabies virus and Japanese encephailitis virus. It presents a unique host target for broad-spectrum antiviral activity.

Although HBV is a DNA virus, it uses a pregenomic RNA template for the initiation of DNA synthesis and potentially therefore RIG-I may be a receptor for HBV pgRNA. The present inventors have discovered that certain dinucleotide compounds have potential for stimulation of innate immunity and induction of interferon production through activation of RIG-I pathway. Such compounds may also be useful prophylactically against viral infections and useful as adjuvants in vaccines.

The viral sensor RIG-I is a multimeric cytosolic protein consisting of a C-terminal regulatory domain (RD), two terminal caspase activation and recruitment domains (CARDS), as well as, a central ATPase domain. Viral double-stranded RNA (dsRNA) and 5'-triphosphate are two PAMPs that enable RIG-I to discriminate pathogenic RNA (dsRNA with and without triphosphate) from host RNA (which usually has a "Cap" modification at the end). Furthermore, RIG-I has the ability to sense viral RNA through the phenomenon of translocation (Myong et al., Science 323, 1070. 2009). The RIG-I translocation and repetitive shuttling on dsRNA of the viral genome is the trigger for RIG-I to undergo conformational change, activate its ATPase, and expose CARDS for ubiquitination. In the next step, CARDS interacts with mitochondrial antiviral signaling (MAVS) [also known as interferon beta stimulator [(IPS-1), or VISA] to elicit downstream signaling that leads to type I IFN expression (IFN-$\alpha$, $\beta$).

NOD2 and RIG-I are multimeric proteins, which are structurally and organizationally very similar. Thus, like RIG-I, NOD2 contains CARD domain. In addition, both RIG-I and NOD2 possess nucleotide-binding pockets located in NBD (nucleotide binding domains) (for NOD2) and helicase (for RIG-I) domains. Molecular modeling studies show that certain dinucleotide compositions are superimposable on nucleotide triphosphate (NTP) structures that bind to NBD. We hypothesize that short oligonucleotides act as NTP mimics that bind to the NBD of NOD2 (and RIG-I) and cause their activation for downstream antiviral action.

Figure 8:
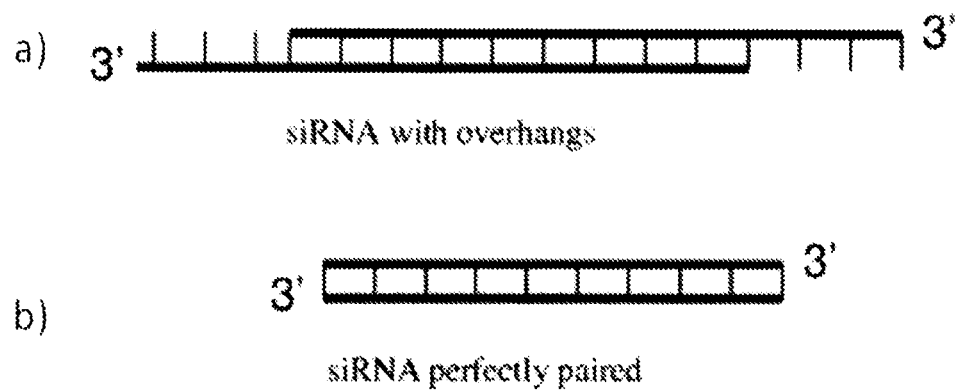
FIG. 8 is a drawing depicting a) an exemplary siRNA with 2-3 nucleotide overhangs and b) an exemplary siRNA with no overhangs.

Further, oligonucleotide compositions comprising antisense compounds capable of RNA interference and microRNA compounds have been utilized to downregulate the expression of a target protein by the inhibition of translation of the corresponding target messenger RNA (see, e.g., Iyer, R. P. et al., *Drugs of the Future*, 2003, 28, 51-59; Mirabelli, C. T. et al., S. T. *Crooke and B. Lebleu (Eds.*,) CRC Press, New York 1993, 7-35; and Szymkowski, D. E. et al, *Drug Disc. Today*, 1996, 1, 415-28). Exemplary siRNAs capable of mediating RNAi are shown in FIG. 8. The mechanisms of hybridization-induced inhibition of a target messenger RNA are well known in the art. It has also been recognized that these compounds may hybridize to other off-target messenger RNA and inhibit the production of proteins.

The nucleic acids may also interact with the viral sensors such as TLR, RIG-I, NOD2 and so on and cause off-target effects resulting in side effects and toxicities. In certain instances, olignucleotide compositions have been designed as Aptamers, which are intended to bind specifically with a target aberrant protein and block its activity. In other cases, certain oligonucleotide compositions contain specific structural motifs (e.g. CpG motifs) that are known to stimulate immune pathways. In all these intended therapeutic applications of oligonucleotides, they produce sequence-specific and sequence non-specific side effects and "off-target" effects.

It has been the existing paradigm that besides, specific compositions for RNAi and antisense activity and/or to stimulate immune pathways, oligonucleotides should have ideally a chain length of 18 to 26 nucleotides. For example, for RNA interference induced by siRNA, each segment of the double-stranded RNA should be between 19 to 28 nucleotides long. For antisense applications, the chain length for single-stranded oligonucleotides should be around 19 to 21 nucleotides long. However, we have found that shorter oligonucleotide fragments have complex biological effects, These short fragments could result from metabolism of longer oligonucleotides, which is mediated by exo and endonucleases present in cells. These shorter fragments with specific structural attributes may activate certain immune pathways by interacting with RIG-I, NOD, or TLR receptors present in cells. Such interactions can produce off-target effects due to downstream effects such as the induction of chemokines and cytokines expression as well as pro-, and anti-inflammatory factors. Consequently, the off-target effects and side effects associated with longer oligonucleotides may be associated with that resulting from the metabolite fragments such as di, tri, tetranucleotides etc interacting with cellular proteins and receptors. Hence the off-target effects could be minimized by rational choice of natural or chemically modified segments within the oligonucleotide.

The invention relates to design of nucleotide compositions for the optimal design of oligonucleotides (antisense and siRNA to improve targeting of RNA) and proteins and receptors (aptamers, immunomodulatrory oligonucleotides).

The present inventors have found that certain short oligonucleotide compounds have the potential to stimulate innate immune response and cause activation of IRF3, produce cellular interferons, and induce the production of antimicrobial peptides. In certain instances, it is believed that some di-, and trinucleotide compounds are capable of stimulating innate immune response.

Definitions

The term "antimicrobial" is meant to denote compounds that are effective against viral, bacterial, fungal and parasitic infections.

The term "cancer" refers to a malignant tumor of potentially unlimited growth that expands locally by invasion and systemically by metastasis.

The term "aryl," as used herein, refers to a mono- or polycyclic carbocyclic ring system having one or two aromatic rings including, but not limited to, phenyl, naphthyl, tetrahydronaphthyl, indanyl, idenyl and the like.

The term "heteroaryl," as used herein, refers to a mono- or polycyclic (e.g. bi-, or tri-cyclic or more) aromatic radical or ring having from five to ten ring atoms of which one or more ring atom is selected from, for example, S, O and N; zero, one or two ring atoms are additional heteroatoms independently selected from, for example, S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

In accordance with the invention, any of the aryls, substituted aryls, heteroaryls and substituted heteroaryls described herein, can be any aromatic group. Aromatic groups can be substituted or unsubstituted.

The term "alkyl," as used herein, refer to saturated, straight- or branched-chain hydrocarbon radicals containing between one and six, or one and twelve carbon atoms, respectively. Examples of $C_1$-$C_6$ alkyl radicals include, but are not limited to, methyl, ethyl, propyl, isopropyl, n-butyl, tert-butyl, neopentyl and n-hexyl radicals; and examples of $C_1$-$C_{12}$ alkyl radicals include, but are not limited to, ethyl, propyl, isopropyl, n-hexyl, octyl, decyl, dodecyl radicals.

The terms "aralkyl" or "arylalkyl" embrace aryl-substituted alkyl radicals such as benzyl, diphenylmethyl, triphenylmethyl, phenylethyl, and diphenylethyl.

The term "heterocyclic" or "heterocyclyl" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "cycloalkyl," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl.

The terms "substituted aryl", "substituted alkyl," "cycloalkyl", as used herein, refer to aryl, alkyl and cycloalkyl groups as previously defined, substituted by independent replacement of one, two, or three or more of the hydrogen atoms thereon with substituents including, but not limited to, —F, —Cl, —Br, —I, —OH, protected hydroxyl, —$NO_2$, —CN, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$O_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkenyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "steroidal", as used herein, refers to any of numerous naturally occurring or synthetic fat-soluble organic compounds having as a basis 17 carbon atoms arranged in four rings and including the sterols and bile acids, adrenal and sex hormones, certain natural drugs such as digitalis compounds, and the precursors of certain vitamins. Examples of steroidal structure includes, but not limited to, cholesterol, cholestanol, 3α-cyclo-5-α-cholestan-6-β-ol, cholic acid, cholesteryl formate, cholestanyl formate.

The term "modified nucleoside", as used herein, refers to any nucleoside that includes a modified heterocyclic base, a modified sugar moiety, or a combination thereof. In some embodiments, the modified nucleoside is a non-natural pyrimidine or purine nucleoside, as herein described. Examples of the modified nucleoside include, but not limited to, 2'-substituted ribonucleoside an arabinonucleoside or a 2'-deoxy-2'-flouroarabinoside, deaza-adenine, deazaguanine.

The term "modulate" refers to increases or decreases in a parameter in response to exposure to a compound of the invention.

For purposes of the invention, the term "short oligonucleotide(s)" (SMNH) refers to a mono, di or polynucleoside formed from 1 to about 6 linked nucleoside units. Such short oligonucleotides can be obtained from existing nucleic acid sources, including genomic or cDNA, but are preferably produced by synthetic methods. The nucleoside residues can be coupled to each other by any of the numerous known internucleoside linkages. Such internucleoside linkages may be modified or unmodified and include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "short nucleotide" also encompasses polynucleosides having one or more stereospecific internucleoside linkage (e.g., ($R_P$)- or ($S_P$)-phosphorothioate, alkylphosphonate, or phosphotriester linkages. The short nucleotides of the invention include any such internucleoside linkage, whether or not the linkage comprises a phosphate group. In certain preferred embodiments, these internucleoside linkages may be modified or unmodified and include without limitation, phosphodiester, phosphorothioate, or phosphorodithioate linkages, or combinations thereof.

The term "short nucleotide(s)" also encompasses additional substituents including, without limitation, protein groups, lipophilic groups, intercalating agents, diamines, folic acid, cholesterol and adamantane.

The term "short nucleotide(s)" also encompasses any other nucleobase containing polymers, including, without limitation, peptide nucleic acids (PNA), peptide nucleic acids with phosphate groups (PHONA), locked nucleic acids (LNA).

Examples of PNA and LNA are shown below:

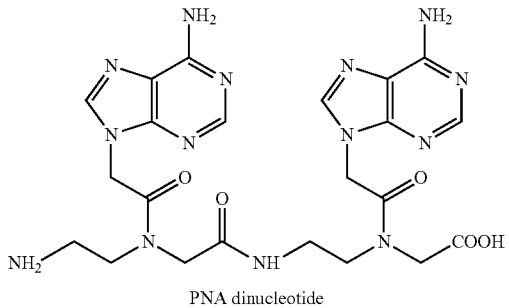

PNA dinucleotide

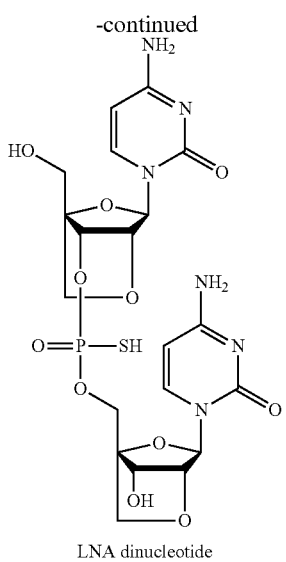

LNA dinucleotide

A "nucleotide" refers to a sub-unit of a nucleic acid [(whether DNA or RNA or analogue thereof such as peptide nucleic acid (PNA) and locked nucleic acid (LNA)], which includes an internucleotide linkage, a sugar group and a heterocyclic base, as well as analogs of such sub-units. A "nucleoside" references a nucleic acid subunit including a sugar group and a heterocyclic nucleobase. It will be appreciated that, as used herein, the terms "nucleoside" and "nucleotide" will include those moieties which contain not only the naturally occurring internucleotide linkages (with respect to "nucleotides") such as phosphodiester internucleotide linkage; naturally occurring sugar moieties such as a ribose and deoxyribose moieties; and naturally occurring nucleobases such as purine and pyrimidine bases, e.g., adenine (A), thymine (T), cytosine (C), guanine (G), or uracil (U), but also modified internucleotide linkages, modified sugar moieties and modified purine and pyrimidine bases or analogs thereof or any combination of modified and unmodified internucleotide linkage, sugar moiety and purine and pyrimidine bases. Other examples of modified nucleosides include acyclonucleosides, which consists of ring-opened versions of the ribose and deoxyribose moieties. Correspondingly, such ring-opened nucleosides may be used in forming modified nucleotides. Other examples of modified nucleosides include C-nucleosides such as pseudo-isocytidine, and nucleoside mimics including nucleoside isosteres such as peptide nucleic acid monomers, and locked nucleic acid monomers.

The term "subject" includes organisms which are capable of suffering from a condition or disease as described herein. The subject may be human and non-human animals, a cell, or any living organisms (such as, virus, fungus, micro-organism). Human animals include human patients suffering from or prone to suffering from a condition or disease, as described herein. Non-human animals includes all vertebrates, e.g., mammals, e.g., rodents, e.g., mice, and non-mammals, such as, non-human primates, also sheep, dog, cow, chickens, amphibians, and reptiles. A living organism is any contiguous living system (such as animal, fungus, micro-organism etc.). In at least some form, all organisms are capable of response to stimuli, reproduction, growth and development, and maintenance of homoeostasis as a stable whole.

Abbreviations

Abbreviations as used in the application, are provided as follows:

AcOH stands for acetic acid;
Boc$_2$O stands for di-tert-butyl-dicarbonate;
Boc stands for t-butoxycarbonyl;
Bpoc stands for 1-methyl-1-(4-biphenylyl)ethyl carbonyl;
Bz stands for benzoyl;
Bn stands for benzyl;
BocNHOH stands for tert-butyl N-hydroxycarbamate;
t-BuOK stands for potassium tert-butoxide;
Bu$_3$SnH stands for tributyltin hydride;
CDI stands for carbonyldiimidazole;
CH$_2$Cl$_2$ stands for dichloromethane;
CH$_3$ stands for methyl;
CH$_3$CN stands for acetonitrile;
DMSO stands for dimethyl sulfoxide;
EtOAc stands for ethyl acetate;
EtOH stands for ethanol;
Et$_2$O stands for diethyl ether;
HCl stands for hydrogen chloride;
MeOH stands for methanol;
MOM stands for methoxymethyl;
Ms stands for mesyl or —SO$_2$—CH$_3$;
Ms$_2$O stands for methanesulfonic anhydride or mesyl-anhydride;
NaCl stands for sodium chloride;
NaH stands for sodium hydride;
NaHCO$_3$ stands for sodium bicarbonate or sodium hydrogen carbonate;
Na$_2$CO$_3$ stands for sodium carbonate;
NaOH stands for sodium hydroxide;
Na$_2$SO$_4$ stands for sodium sulfate;
NaHSO$_3$ stands for sodium bisulfite or sodium hydrogen sulfite;
Na$_2$S$_2$O$_3$ stands for sodium thiosulfate;
NH$_2$NH$_2$ stands for hydrazine;
NH$_4$HCO$_3$ stands for ammonium bicarbonate;
NH$_4$Cl stands for ammonium chloride;
OH stands for hydroxyl;
OMe stands for methoxy
OEt stands for ethoxy
TEA or Et$_3$N stands for triethylamine;
TFA stands for trifluoroacetic acid;
THF stands for tetrahydrofuran;
TPP or PPh$_3$ stands for triphenylphosphine;
Ts stands for tosyl or —SO$_2$—C$_6$H$_4$CH$_3$;
Ts$_2$O for tolylsulfonic anhydride or tosyl-anhydride;
TsOH stands for p-tolylsulfonic acid;
Ph stands for phenyl;
TBS stands for tert-butyl dimethylsilyl; or
TMS stands for trimethylsilyl;
TMSCl stands for trimethylsilyl chloride.

Compounds

In one aspect, the invention provides a compound of formula (I):

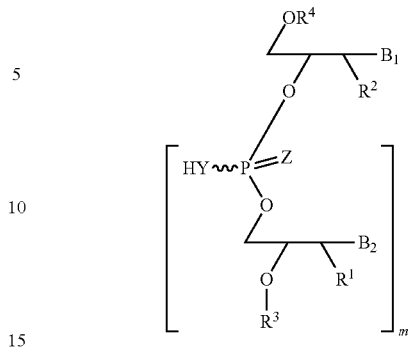

formula (I)

or pharmaceutically acceptable salts, racemates, enantiomers, diastereomers, geometric isomers, or tautomers thereof,
wherein
$R^1$ and $R^2$, each independently, are H, OH, —O-akyl, alkyl, substituted alkyl, cycloalkyl, aryl, substituted aryl, aralkyl, heterocyclyl, —O-aryl, or O-heteroarylaryl;
$R^3$ is selected from hydrogen, alkyl, substituted alkyl, —C(O)-alkyl, —C(O)O-alkyl, —C(O)-aryl, —C(O)O-aryl, —C(O)NH-alkyl, and —C(O)NH-aryl;
Y and Z, each independently, are O or S;
$B_1$ and $B_2$, on each occurrence, independently are adeninyl, guaninyl, thyminyl, cytosinyl, uracil, or a modified nucleoside moiety;
m=1, 2, 3, 4, 5, or 6;
$R^4$, on each occurrence, independently is a monophosphate, diphosphate, or triphosphate group
In one embodiment, the compound of formula (I) is not Compound 5.
In another aspect, the invention provides a compound of formula (II):

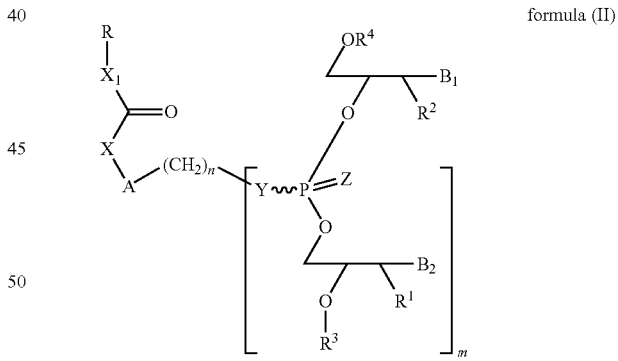

formula (II)

or pharmaceutically acceptable salts, racemates, enantiomers, diastereomers, geometric isomers, or tautomers thereof,
wherein
X=absent, O, NH, NR, or S;
$X_1$=absent, O, or NH;
A=absent, aryl, or aralkyl;
n=0, 1, 2, 3, 4, or 5;
R=alkyl, substituted alkyl, cycloalkyl, aryl, substituted aryl, aralkyl, heterocylyl, —O-alkyl, —O-heteroaryl, or steroidal;
$R^1$ and $R^2$, each independently, are H, OH, —O-akyl, alkyl, substituted alkyl, cycloalkyl, aryl, substituted aryl, aralkyl, heterocyclyl, —O-aryl, or —O-heteroarylaryl;

$R^3$ is selected from hydrogen, alkyl, substituted alkyl, —C(O)-alkyl, —C(O)O-alkyl, —C(O)-aryl, —C(O)O-aryl, —C(O)NH-alkyl, and —C(O)NH-aryl;

Y and Z, each independently, are O or S;

$B_1$ and $B_2$, on each occurrence, independently are adeninyl, guaninyl, thyminyl, cytosinyl, uracil or a modified nucleoside moiety;

m is 1, 2, 3, 4, 5, or 6;

$R^4$, on each occurrence, independently is a monophosphate, diphosphate, or triphosphate group.

In one embodiment, the compound of formula (II) is not Compound 6k. In another embodiment, $R^4$ is not H when m is 2.

A nucleoside unit is represented by the internationally accepted convention of line drawing. In the example below a 2'-substituted ribonucleoside is represented in both the conventional structure and the corresponding line drawing format

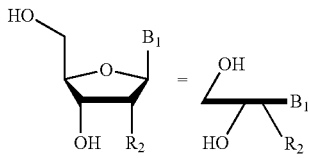

In certain instances, the compound of the invention is Compound 5 or Compound 6k.

The sugar units attached to $B_1$ and $B_2$ that give rise to α or βN- or C-nucleoside includes, but not limited to, furanose, deoxyribofuranose, ribose, and arabinose.

In certain embodiments, compounds of the invention comprise one or more modifications on "natural" nucleic acids, i.e., natural internucleosidic linkages, or nucleobases G, C, T, U, A and etc. Modifications include, for example, modifications of the internucleotidic linkage, the base, or the sugar moiety of the "natural" nucleic acids.

Nucleobases include naturally occurring purine and pyrimidine nucleobases and modified nucleobases that include but are not limited to methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N-6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl) uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, 2,6-diaminopurine 5-trifluoromethyl thymine, 6-chloro-adenine, 7-deaza-adenine. Other examples without limitation include 5-fluoro-Uracil, 5-trifluoromethyl Thymine, 6-choro-Adenine, 2-cyclopentyloxy-Adenine, 7-deaza-Adenine.

In certain embodiments, the base may be unnatural nucleobases including the universal nucleobases. Such examples of base without limitation include difluorotolyl, nitropyrrolyl and nitro-imidazolyl and so on.

It should also be understood that a "modified base" also referred to as a "modified nucleobase", includes a nitrogen containing compound that may or may not be heterocyclic. Such preferred nitrogen containing compounds include but are not limited to —NHR18 wherein R18 is hydrogen, butyloxycarbonyl (Boc), benzyloxycarbonyl, allyl, substituted or unsubstituted alkyl, substituted or unsubstituted cycloalkyl, substituted or unsubstituted aralkyl, substituted or unsubstituted aryl, substituted or unsubstituted heteroaryl, or heterocyclic.

The term "modified nucleobase" is further intended to include heterocyclic compounds that are not nucleosidic bases in the most classical sense but that can serve as nucleosidic bases. Such compounds include "universal bases" as are known in the art. Universal bases may include an aromatic ring moiety, which may or may not contain nitrogen atoms. In some embodiments, a universal base may be covalently attached to the C-1' carbon of a pentose sugar of the nucleoside. Examples of universal bases include 3-methyl-propynylcarbostyryl (PIM), 3-methylisocarbostyryl (MICS), and 5-methyl isocarbostyryl moieties. Additional examples include Inosine derivatives, azole carboxamide analogues, nitroazoles, and nitroimidazoles.

Examples of modified nucleotide and nucleoside sugar moieties include but are not limited to: trehalose, arabinose, 2'-deoxy-2'-substituted pentose moiety, 2'-O-substituted pentose moiety, ribose, lyxose, and xylose, or hexose sugar group. For purposes of the invention, the term "2'-substituted" of any of the named sugar groups such as "2'-substituted ribonucleoside" or "2'-substituted arabinoside" includes ribonucleosides or arabinonucleoside in which the hydroxyl group at the 2'-position of the pentose moiety is substituted to produce a 2'-substituted or 2'-O-substituted ribonucleoside or arabinonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-O-methylribonucleo sides (also indicated herein as 2'-OMe) or 2'-O-methylarabinosides and 2'-O-methoxyethylribonucleosides or 2'-O-methoxyethylarabinosides. The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides.

Examples of modified internucleotide linkages include but are not limited to: substituted and unsubstituted phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. Substitutions of modified and unmodified internucleotide linkages include the following moiety:

The compounds of the present invention may contain one or more asymmetric centers and can thus occur as racemates and racemic mixtures, single enantiomers, diastereomeric mixtures and individual diastereomers. The present invention is meant to include short nucleotide compounds having the β-D stereochemical configuration for the five-membered furanose ring, that is, short nucleotide compounds in which the substituents at C-1 and C-4 of the five-membered furanose ring have the β-stereochemical configuration ("up" orientation which is typically denoted by a bold line in some formulas depicted herein).

In certain embodiments, the compounds of this invention can modulate immune-stimulatory pathways, such as, Toll-like receptors (TLR), as well as, non-TLR pathways, such as, those involving the activation of the Retinoic acid inducible gene-1 (RIG-I), and Nucleotide oligomerization proteins (NOD). It is known that the activation of these pathways by their respective ligands can induce the production of various cytokines, and chemokines such as Interleukins, Interferons and also cause induction of certain cellular proteins thereby providing antimicrobial immunity.

In another aspect, the invention relates to the design of compounds that are capable of inhibiting the inflammatory pathways. The invention also relates to the synthesis of the specifically designed compounds. The compounds as designed and synthesized have beneficial effects in autoimmune diseases.

In certain embodiments, the compounds of the invention have therapeutic utility against a variety of diseases, including viral diseases, autoimmune diseases (such as allergy, asthma, inflammatory disorders), and cancer.

In certain embodiments, the compounds of this invention act as activators of intracellular microbial sensors and cause activation of immune response. The compounds showed antiviral activity against DNA virus (HBV) and RNA viruses such as HCV and RSV. It is believed that the claimed compounds can be used not only to induce immune response as agonists and can also be used to block (antagonize) undesired immune response in auto-immune diseases.

Pharmaceutical Compositions

The present invention also relates to pharmaceutical compositions comprising one or more compounds of the invention, or derivatives thereof, and a pharmaceutically acceptable carrier. In one embodiment, the invention provides a pharmaceutical composition made by combining any of the compounds described above and a pharmaceutically acceptable carrier.

The pharmaceutical compositions of the present invention comprise at least one compound of the invention as an active ingredient or a pharmaceutically acceptable salt thereof, and may also contain a pharmaceutically acceptable carrier and excipients and optionally other therapeutic ingredients. By "pharmaceutically acceptable" is meant that the carrier, diluent, or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well known in the art of pharmacy.

In certain embodiments, the compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin.

When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. Various stabilizers may be added that would stabilize the active pharmaceutical ingredient against degradation, such as amino acids or polyamines. Other excipients could include without limitation PEG 400, glycine, Vitamin E derivatives, Sorbitan mono-oleate, Chitosan, Choline citrate, Sorbitan monostearate, Tween 80, Igepal CA 630, Brij 35, NP-40 and their analogous derivatives.

Compounds of the invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous repa-ration of sterile injectable solutions or dispersions. In all cases, the form is preferably sterile and is preferably fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human with a therapeutically effective dosage of a compound of the present invention. The terms "administration of" and "administering a" compound should be understood to mean providing a compound of the invention to the individual in need. The routes of administration include for example without limitation oral, sublingual, transmucosal, intravenous, subcutaneous, intranasal, topical, vaginal, etc.

The compounds mentioned in formula 1-2 are useful in a broad range of therapeutic areas that involve host immune components including but not limited to: allergy, inflammation, autoimmune diseases, COPD, asthma and so on. By virtue of the fact that these compounds can act as modulators of immune response through a number of mechanisms, they will have therapeutic use in autoimmune diseases. For example, since the compounds have the potential to stimulate innate immune response, they can be utilized either alone or in combination with other agents in the treatment of a variety of cancers including but not limited to melanoma, myeloma, carcinoma, glioblastoma and sarcoma. For example, since certain oligonucleotide compositions have the potential to inhibit immune response, they can be utilized either alone or in combination with other agents in the treatment of a variety of autoimmune diseases including, but not limited to, allergy, asthma, COPD and multiple sclerosis.

The methods of treatment of the present invention, consists of administering to the subject a therapeutically effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "therapeutically effective amount" of a compound of the invention, as used herein, mean a sufficient amount of the compound so as to produce a beneficial biological response in a biological sample or in a subject. As well understood in the medical arts, a therapeutically effective amount of a compound of this invention will be at a reasonable benefit/risk ratio applicable to any medical treatment.

An inhibitory amount or dose of the compounds of the present invention may range from about 0.1 mg/Kg to about 500 mg/Kg, alternatively from about 1 to about 50 mg/Kg. Inhibitory amounts or doses will also vary depending on route of administration, as well as the possibility of co-usage with other agents.

The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, brain and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms. It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single, multiple or in divided doses can be in amounts, for example, from 0.01 to 50 mg/kg body weight or more usually from 0.1 to 25 mg/kg body weight.

Single dose compositions may contain such amounts or submultiples thereof to make up the daily dose. Multiple doses may be single doses taken at different time intervals. In general, treatment regimens according to the present invention comprise administration to a patient in need of such treatment from about 10 mg to about 1000 mg of the compound(s) of this invention per day in single or multiple doses.

In one aspect, the invention provides a kit for treating, modulating, or preventing a condition or disease as described herein. The kit may include a compound of the invention or its nucleotide segments thereof, and instructions for use the kit. The instructions for use may include information on dosage, method of delivery, storage of the kit, etc. The kits may also include, reagents, for example, test compounds, buffers, media (e.g., cell growth media), cells, etc. Test compounds may include known compounds or newly discovered compounds, for example, combinatorial libraries of compounds.

Combination Therapies

Another aspect of the invention relates to a method of treating a subject with a compound of the invention in combination with one or more agents useful for treating a disease. For example, such agents active against viruses include, Lamivudine (3TC), Adefovir, Tenofovir, Gancyclovir, acyclovir, Interferon, Ribavirin, Telbivudine; other agents against COPD, asthma, allergy allergic rhinitis include, but are not limited to Theophylline, Alvesco (Ciclesonide), Patanase (Olapatidine hydrochloride) Litairis (Ambresentan) (Gilead) Xyzal (Levocetirizine dihydrochloride), Brovana (Arformoterol tartrate), Spiriva(Tritropium bromide) Clarinex, Declomethsone dipropionate, Remodunil (treprostenil), Xopenex, Duoneb(albuterol and Tritropium bromide), Formeterol fumarate, Tracleer (bosantan), Triamcinolone acetonide, Budesonide, Singulair, Serevent, Tilade (inhaler and nebulizer), Zyflo, Accolate, Cedax, Zyrtec, herceptin. Among anticancer agents for example but not limited to taxol, paclitaxel, cisplatin, Herceptin, Gleevac, Interferon and so on.

In accordance with this method of the invention, the individual components of the combination can be administered separately at different times during the course of therapy or concurrently in divided or single combination forms. The invention is therefore to be understood as embracing all such regimes of simultaneous or alternating treatment, and the term "administering" is to be interpreted accordingly. It will be understood that the scope of combinations of the compounds of this invention with other agents includes in principle any combination with any pharmaceutical composition for treating viral, bacterial, parasitic, fungal infections and so on. When a compound of the invention or a pharmaceutically acceptable salt thereof is, used in combination with a second therapeutic agent, the dose of each compound may be either the same as or different from the dose when the compound is used alone.

It is understood that the scope of combinations of the compounds of this invention with other agents includes in principle any combination with any pharmaceutical composition for treating COPD, asthma, allergic rhinitis, cancer and so on. When a compound of the present invention or a pharmaceutically acceptable salt thereof is, used in combination with a second therapeutic agent, the dose of each compound may be either the same as or different from the dose when the compound is used alone.

It is to be noted that several antimicrobial peptides are induced upon immune stimulation by compounds of chemical compositions described herein. Examples include without limitation the antimicrobial peptide called extra-erythrocytically expressed hemoglobin (EEHP).

EXEMPLIFICATION OF THE INVENTION

The following examples are put forth so as to provide those of ordinary skill in the art with a complete disclosure and description of how to make and/or use the compounds, assays, screening, and therapeutic methods of the invention, and are not intended to limit the scope of what the inventors regard as their invention.

Certain examples below illustrate the antiviral activity of a compound of the invention. And, some examples illustrates the correlation between antiviral activity and intracellular production of antiviral peptide.

I. Chemical Examples

Synthesis and Methods of Preparation

Compounds of the invention can be synthesized by methods described in this section, the examples, and the chemical literature (such as, Iyer, R. P. et al., *Antimicrob. Agents Chemother.* 48(6): 2199-2205, 2004; Iyer, R. P. et al., *Antimicrob Agents Chemother.* 48(6):2318-20, 2004; Jin, Y. et al., *Bioorg. Med. Chem. Lett.* 10, 1921-25, 2000; Jin, Y. et al., *Bioorg. Med. Chem. Lett.* 11, 2057-2060, 2001; Iyer, R. P. et al., Current Protocols Unit 3.13, (Beaucage et al Eds,) John Wiley and Sons, 2006; Padmanabhan, S. et al., *Tet. Lett.* 46, 343-347, 2005; and Iyer, R. P. et al., *Organic Preparations & Procedure International,* 37, 205-212, 2005).

Both solid-phase synthesis and solution phase strategies may be used to prepare library of nucleotide analogs. The methods can be used for the synthesis of libraries with modifications at the sugar nucleobase and internucleotidic linkages.

Further, the present inventors have made several technology innovations which facilitated the synthesis of nucleotide libraries: a) Strategies have developed for the synthesis of dinucleotide libraries using solid-phase phosphoramidite and H-phosphonate technologies b). Recent technology innovations were applied for the solid-phase synthesis of dinucleotide compounds and analogs (see literature cited above). These recent technology innovations include, for example, (i) ultra-fast preparation of amino-, and carboxy-functionalized solid-supports using microwave-assisted methods; (ii) novel methods for the loading of nucleosides on solid supports. An improved process for the large-scale preparation of nucleoside-loaded support has been developed. This process involves the use of dimethylformamide (DMF) as a solvent. High nucleoside loadings of 80 to 300 micromol/g of support are obtained; and (iii) a novel reactor called LOTUS® for loading of solid supports and solid-phase synthesis that facilitates large-scale synthesis of dinucleotides. LOTUS® is a multi-purpose reactor equipped with pneumatic valves for controlled delivery of reactants (20-22)

Illustrative synthetic protocols are shown for Compounds 5 and 6k

Example 1

Synthesis of Compound 5

The $R_p,S_p$ mixture of the phosphorothioate analog 3-dApsU$_{2'-OMe}$ (5), was synthesized in large scale (I millimol of nucleoside-loaded controlled-pore glass (CPG) support) using solid-phase phosphoramidite chemistry, (Beaucage, S. L.; Iyer, R. P. *Tetrahedron* 1993, 49, 1925) in conjunction with a specially fabricated LOTUS Reactor® (Padmanabhan, S.; Coughlin, J. E.; Iyer, R. P. *Tetrahedron Lett.* 2005, 46, 343; Iyer, R. P.; Coughlin, J. E.; Padmanabhan, S. *Org. Prep. Proc. Intl.* 2005, 37, 205). The dA-linked CPG support was prepared using our recently discovered ultrafast functionalization and loading process for solid supports. For the sulfurization of the internucleotidic dinucleoside phosphite coupled product, a solution of 3H-1,2-benzodithiole-3-one-1,1,-dioxide (0.4 M in dry CH$_3$CN) was employed (Iyer, R. P.; Regan, J. B.; Egan, W.; Beaucage, S. L. *J. Am. Chem. Soc.* 1990, 112, 1253). Following processing, chromatographic purification, and lyophilization, the sodium salt of $R_p,S_p$ 5 (60:40 mixture) was obtained >96% pure, which was characterized by $^{31}$P and $^1$H NMR.

Thus, solid-phase synthesis of focused library of dinucleotide compounds and analogs was readily performed. In a complementary strategy, solution-phase synthesis was also used for the synthesis of Compound 5. These methodologies enabled the synthesis of compounds with a variety of chemical modifications.

Example 2

Synthesis of Compound 6k

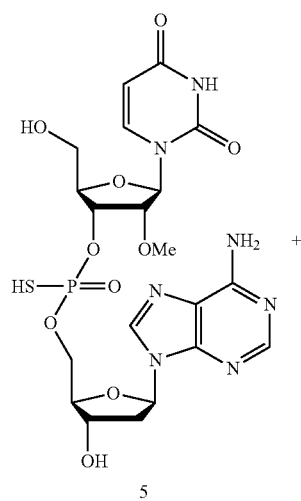

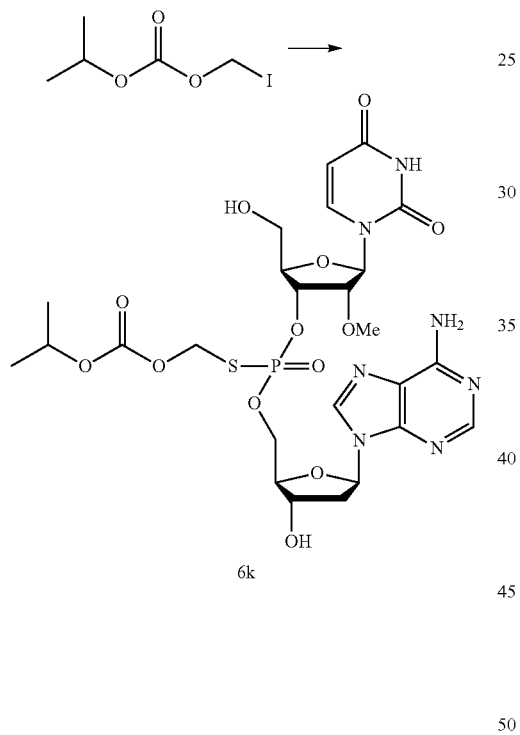

The target Compound 6k was prepared in two steps as follows:

Step 1. Preparation of Iodomethylisopropyl carbonate: To a solution of anhydrous sodium iodide (6 g, 40 mmol) in anhydrous acetonitrile (20 mL) chloromethyl isopropyl carbonate (2.9 g, 19 mmol) in anhydrous. acetonitrile (10 mL) was added drop wise over 20 min. The reaction mixture, covered with aluminum foil (protected from light) was stirred at room temperature overnight. The solid separated was filtered, washed with acetonitrile and the filtrate was concentrated under reduced pressure. Residue was dissolved in water (10 mL) and organics were extracted in ether (25 mL). Ether extracts were washed with sodium bisulfite (5%, 10 mL), later brine (10 mL). Organic layer was dried over anhydrous. sodium sulfate, filtered, concentrated and dried under high vacuum. Yield 2.72 g (58%); $^1$H-NMR δ1.3 (d, 6H), 4.95 (m, 1H), 5.95 (s, 2H).

Step 2. Alkylation of Compound 5. To a solution of Compound 5 (60 mg, 0.098 mmol) in water (HPLC, 400 mL) under stiffing a solution of iodomethyl isopropyl carbonate (80 mg, 0.0166 mmol, 3.33 eq) in acetone (1 mL) was added. Additional acetone (1 mL) was added to get a clear solution to avoid any separation of oily globules of alkylating agent. The reaction mixture, covered in aluminum foil, was stirred for 3 h, concentrated under rotavap conditions and later in high vacuum to obtain the reaction mixture as a white solid. This was purified by silica column chromatography using initially chloroform and slowly with chloroform containing 2% to finally 8% methanol. The fractions, containing major component, were combined, concentrated and dried under high vacuum overnight. The desired pure product Compound 6K was isolated in almost quantitative yield (68 mg); $^{31}$P-NMR (MeOH-$d_4$) δ27.7, 28.6.

II. BIOLOGICAL EXAMPLES AND DESIGN OF THE COMPOUNDS

Example 1

Anti-HBV activity of Compound 6k in the HBV Transgenic Mouse Model

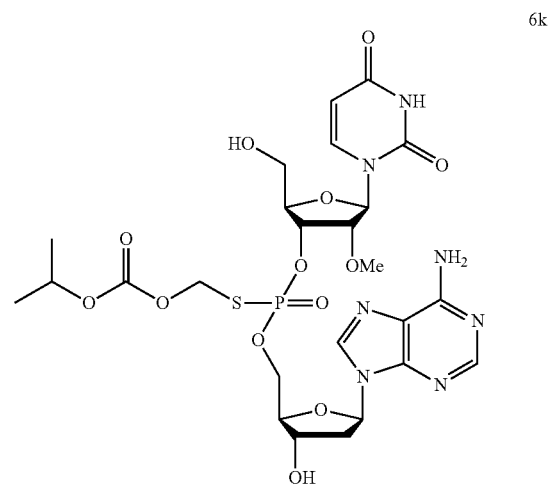

Compound 6k was evaluated for anti-HBV activity in the transgenic mouse model of HBV infection. Male transgenic mouse infected with HBV, with age ranging from 78 to 108 days were used. Compound 6k was initially evaluated at a single dose of 300 mg/kg, administered daily for 14 days by oral gavage. The compounds were administered in citric acid and adefovir dipivoxil was used as a positive control. A control group which received vehicle was used a negative control. Following the treatment, mice were sacrificed and liver tissue analyzed for HBV DNA using Southern blot analysis. The data was statistically evaluated using Kruskall-Wallis nonparametric ANOVA. The test results are provided in the following Table 1.

TABLE 1

| Drug | Dosage (mg/kg/d) | % weight change ± sd | QPCR Liver HBV DNA (pg/μg mean ± sd) | Southern blot Liver HBV DNA (pg/μg mean ± sd) | Liver HBV RNA (log transcripts ± sd) |
|---|---|---|---|---|---|
| 6k | 300 | 4.3 ± 1.8 | 13.3 ± 12 | 5.7 ± 3.2** | 10.8 ± 0.4 |
| ADV | 10 | 5.2 ± 1.5 | 1.7 ± 1.1** | 0.9 ± 1.1*** | 10.5 ± 0.4 |
| Placebo | — | 2.7 ± 2.9 | 65 ± 79 | 57 ± 36 | 10.6 ± 0.5 |

As shown in Table 1, Compound 6k produced up to 2 log reduction of liver HBV DNA compared to untreated control, which was statistically significant with p values 0.01 to 0.001.

Example 2

Effect of Oral Administration of Compounds 6k on Hepatitis B Virus in the HBV Transgenic Mouse Model (a) Male and female transgenic mice (founder 1.3.32) were infected with human hepatitis B virus. Following infection, animals were orally administered Compound 6k, or a placebo of 0.05 M citric acid, pH 2.0 once daily for 14 days. Dosage was 300 mg/kg/d for Compound 6k. The positive control, ADV, was administered at 10 mg/kg/d. The data is summarized in Table 1 (above provided).

Statistical significance is indicated as *P≤0.05, P≤0.01, *P≤0.001 compared to placebo vehicle. The study also established that there was no apparent toxicity of Compound 6k at the high doses employed.

Example 3

Effect of Oral Administration of Compound 6k on Hepatitis B Virus in Transgenic Mice Male and female transgenic mice (founder 1.3.32) were infected with human hepatitis B virus. Following infection, animals were orally administered Compound 6K, or a placebo of 0.05 M citric acid, pH 2.0 once daily for 14 days. Dosages were 100, 10, 5 and 1 mg/kg/d for Compound 6K. The positive control, ADV, was administered at 10 mg/kg/d. The data for Liver HBV DNA in the treated and control groups are summarized in Table 2.

Statistical significance is indicated as *P≤0.05, P≤0.01, *P≤0.001 compared to placebo vehicle. Measurements of serum HBeAg, PEI are reported according to International Immuno Diagnostics standardized assay using Paul Ehrlich International Units (PEI U). The study also established that there was no apparent toxicity at the high doses employed (Table 2).

TABLE 2

Effect of serial doses of Compound 6k on hepatitis B virus in transgenic mice. [b]Effect of oral administration of Compound 6K on hepatitis B virus in transgenic mice.

| | |
|---|---|
| Animals: male and female transgenic mice (founder 1.3.32) | Treatment schedule: qd X 14 d |
| Virus: human hepatitis B virus | Treatment route: p.o. |
| Drug source: Spring Bank | Dosages of 6k: 300, 100, 10, 1 mg/kg/d, ADV 0.1, 0.032 mg/kg/d |
| Technologies, Inc. Placebo: 0.05M citric acid, pH 2.0 | Expt. Duration: 14 days |

| Drug | Dosage (mg/kg/d) | Liver HBV DNA Southern blot[a] (pg/μg mean ± sd) |
|---|---|---|
| 6k | 300 | 4.8 ± 4.4 (2) |
| 6k | 100 | 7.2 ± 8.9 (6) |
| 6k | 10 | 3.4 ± 4.4 (7) |
| 6k | 1 | 16.4 ± 14.7 (6) |
| ADV | 0.10 | 15.6 ± 13.7 (4) |
| ADV | 0.032 | 8.3 ± 11.3 (3) |
| Placebo | — | 24.0 ± 29.3 (15) |

[a]Values from the vehicle group of two studies were combined since they were treated exactly the same.
[b]Ten animals were assigned to each group Example 4

Figure 2:
FIG. 2 shows that the anti-HBV activity of orally administered Compound 6k correlates with EEEH expression in a dose dependent manner in transgenic mouse.

Increased Expression of Extra-Erythrocytically Derived hemoglobin (EEEH) as Antiviral Peptide in Hepatitis B Virus Infected Transgenic Mouse Treated with Compound 6k. Anti-HBV Activity Correlates with the Production of the Antimicrobial Peptide EEEH Protein The plasma and liver samples following the administration of Compound 6k in transgenic mice were collected and SDS PAGE was conducted to evaluate the presence of extra-erythrocytically expressed hemoglobin (EEEH), the antimicrobial peptide, which is induced as part of the activation of the innate immune system. This protein is approximately 15 kilodaltons molecular weight. EEEH expression is shown in FIG. 1 which is an SDS PAGE profile of samples shown in Table 3. As can be seen, the Compound 6k induces dose-dependent expression of EEEH protein. FIG. 2 illustrates that anti-HBV activity of orally administered Compound 6k correlates with EEEH expression in a dose dependent manner.

TABLE 3

Description of samples loaded in SDS PAGE, FIG. 1

| Lane # | Sample | Loading Volume |
|---|---|---|
| 1 | | |
| 2 | Control Mouse plasma No DTT, 1:50 | total volume 10 μL with 0.2 μL of plasma |
| 3 | | |
| 4 | 1 mg of 6k Mouse plasma No DTT 1:50 | total volume 10 μL with 0.2 μL of plasma |

TABLE 3-continued

Description of samples loaded in SDS PAGE, FIG. 1

| Lane # | Sample | Loading Volume |
|---|---|---|
| 5 | | |
| 6 | 10 mg of 6k Mouse plasma No DTT 1:50 | total volume 10 μL with 0.2 μL of plasma |
| 7 | | |
| 8 | 100 mg of 6k Mouse plasma No DTT 1:50 | total volume 10 μL with 0.2 μL of plasma |
| 9 | | |
| 10 | Sigma Mouse plasma No DTT 1:50 | total volume 10 μL with 0.2 μL of plasma |
| 11 | | |
| 12 | Prestained STDs | 5 ul |

Example 5

Kinetics of EEEH Expression in Woodchucks Following Administration of Compound 5 by Sublingual Route Compound 5 was administered by sublingual route to woodchucks, at a dose of 20 g/kg in Transcutol, and blood was drawn periodically for analysis. Test results are provided in Tables 4 and 5 and FIG. 3 and FIG. 4.

TABLE 4

| Lane # | Sample | Loading Volume |
|---|---|---|
| 1 | | |
| 2 | Sublingual Wood Chuck Pool Time Zero, No DTT, 1000:1 | total volume 10 μL with 0.01 μL of plasma |
| 3 | Sublingual Wood Chuck, Pool 5 min No DTT, 1000:1 | total volume 10 μL with 0.01 μL of plasma |
| 4 | Sublingual Wood Chuck, Pool 15 min No DTT, 1000:1 | total volume 10 μL with 0.01 μL of plasma |
| 5 | Sublingual Wood Chuck, Pool 30 min No DTT, 1000:1 | total volume 10 μL with 0.01 μL of plasma |
| 6 | Sublingual Wood Chuck, Pool 1 hr min No DTT, 1000:1 | total volume 10 μL with 0.01 μL of plasma |
| 7 | Sublingual Wood Chuck, Pool 2 hrs No DTT, 1000:1 | total volume 10 μL with 0.01 μL of plasma |
| 8 | Sublingual Wood Chuck, Pool 4 Hrs No DTT, 1000:1 | total volume 10 μL with 0.01 μL of plasma |
| 9 | Sublingual Wood Chuck, Pool 24 Hrs No DTT, 1000:1 | total volume 10 μL with 0.01 μL of plasma |
| 10 | | |
| 11 | | |
| 12 | Pre stained stds | 5 ul |

Figure 3:
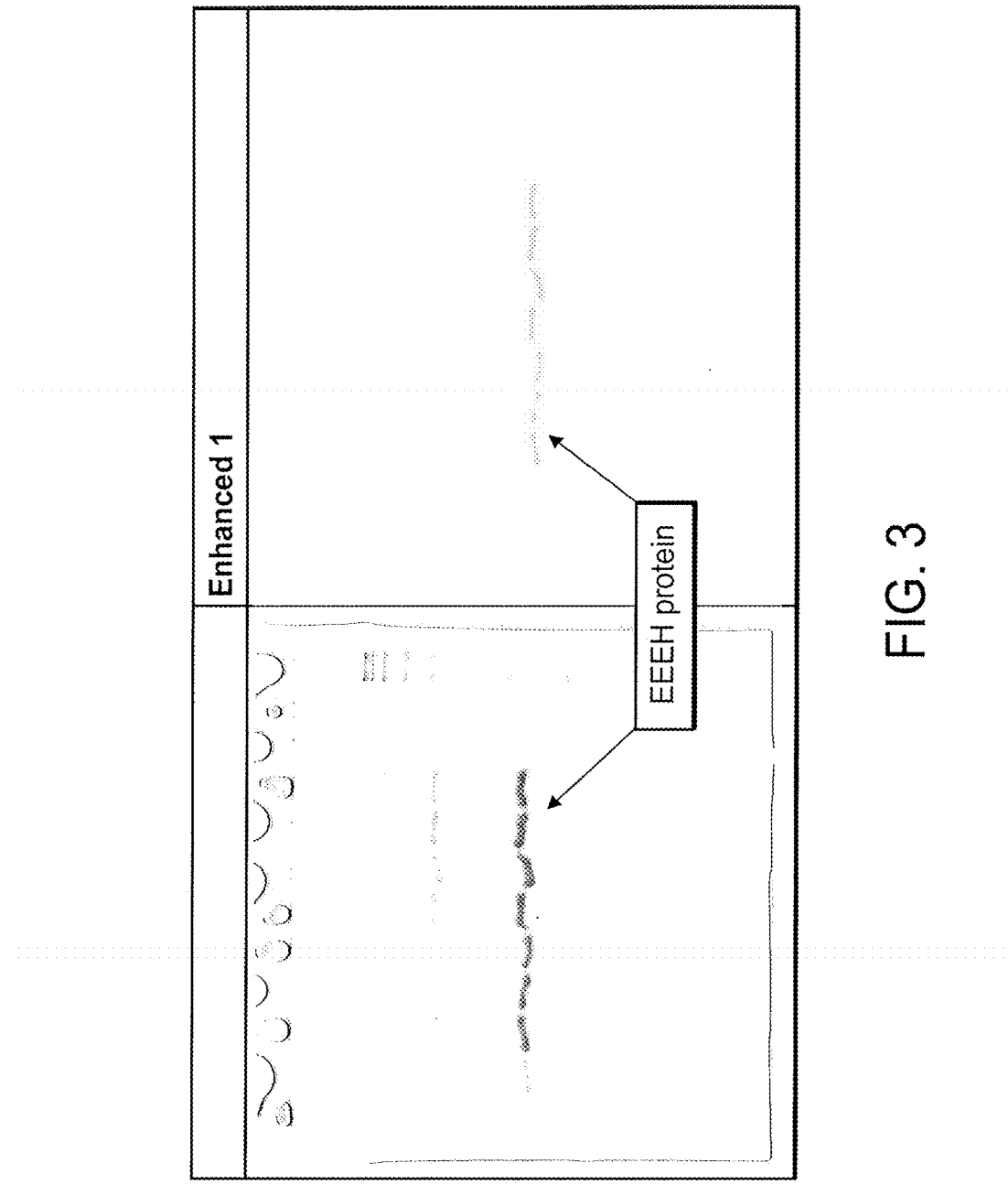
FIG. 3 shows the expression of antimicrobial protein EEEH following sublingual administration of Compound 5.
Figure 4:
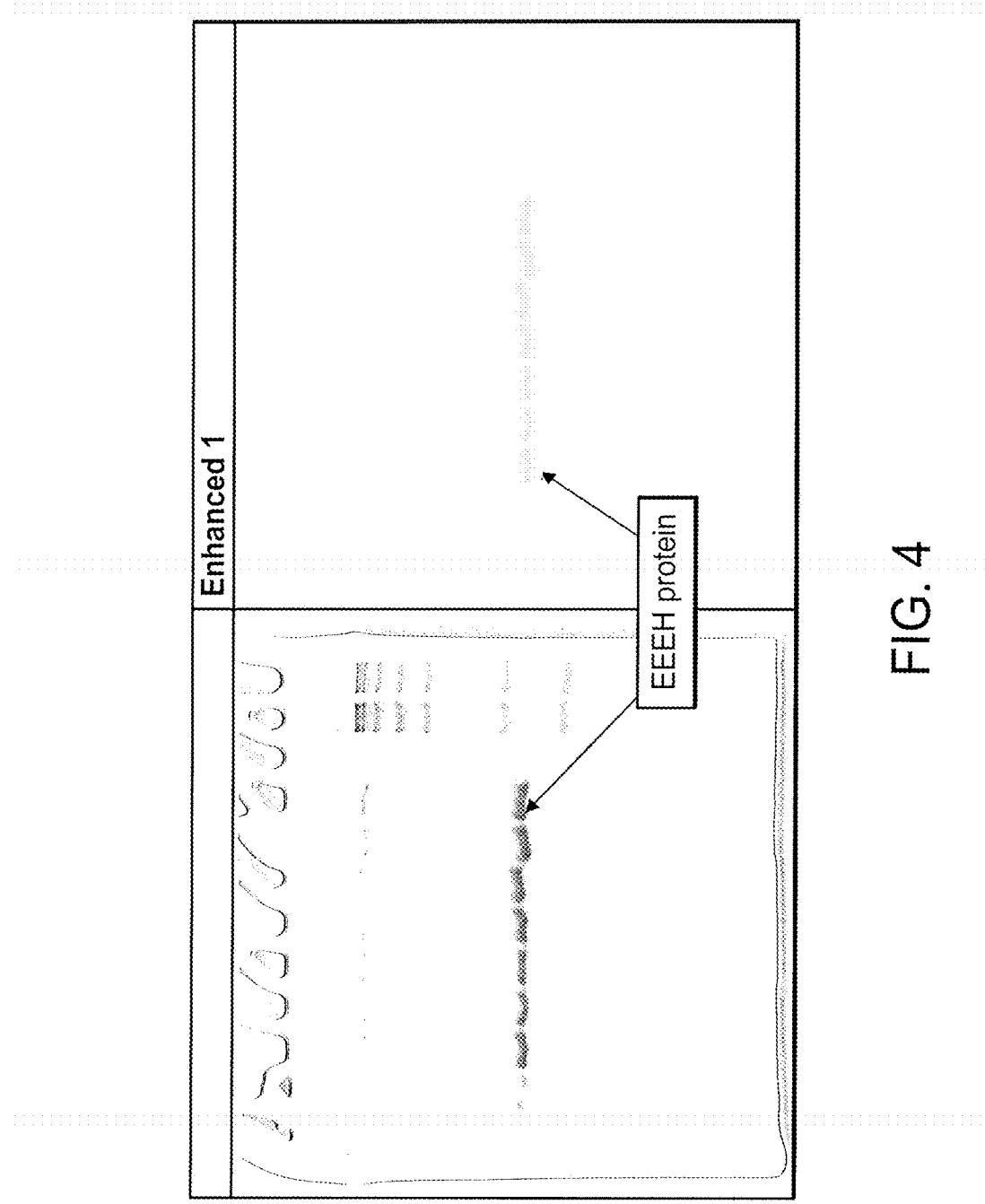
FIG. 4 shows EEEH expression in woodchucks following administration of Compound 5 via sublingual administration.
Figure 5:
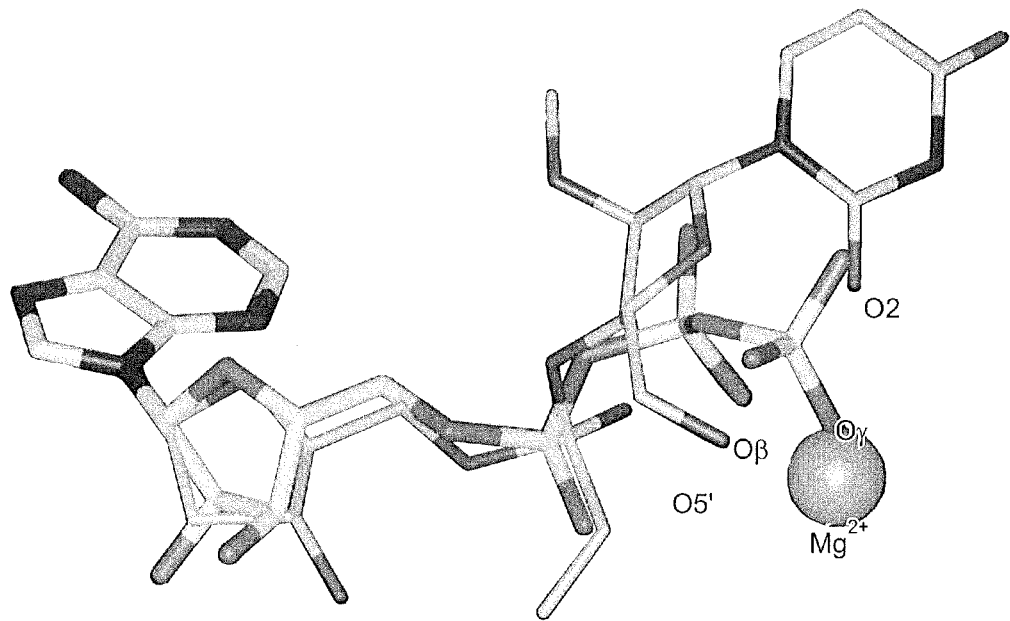
FIG. 5 is a graph generated through molecular modeling, showing that Compounds 5 and 6k are adenosine triphosphate (ATP) mimics.

The results shown in Table 4 and FIG. 3 and FIG. 4 indicate that Compound 5 induces EEEH expression when administered through sublingual route.

TABLE 5

| Lane # | Plasma Sample following administration of 5 | Loading Volume |
|---|---|---|
| 1 | | |
| 2 | Sublingual Wood Chuck Pool Time Zero, DTT, 1000:1 | total volume 10 μL with 0.01 μL of plasma |
| 3 | Sublingual Wood Chuck, Pool 5 min DTT, 1000:1 | total volume 10 μL with 0.01 μL of plasma |
| 4 | Sublingual Wood Chuck, Pool 15 min DTT, 1000:1 | total volume 10 μL with 0.01 μL of plasma |
| 5 | Sublingual Wood Chuck, Pool 30 min DTT, 1000:1 | total volume 10 μL with 0.01 μL of plasma |
| 6 | Sublingual Wood Chuck, Pool 1 hr min DTT, 1000:1 | total volume 10 μL with 0.01 μL of plasma |
| 7 | Sublingual Wood Chuck, Pool 2 hrs DTT, 1000:1 | total volume 10 μL with 0.01 μL of plasma |
| 8 | Sublingual Wood Chuck, Pool 4 Hrs DTT, 1000:1 | total volume 10 μL with 0.01 μL of plasma |
| 9 | Sublingual Wood Chuck, Pool 24 Hrs DTT, 1000:1 | total volume 10 μL with 0.01 μL of plasma |
| 10 | | |
| 11 | PreStained stds | 5 ul |
| 12 | Pre stained stds | 5 ul |

As can be seen from the above, the induction of the EEEH protein is very rapid following absorption of Compound 5 by the sublingual route.

Example 6

EEEH Expression Correlates with RIG-I Translocation on Double-Stranded RNA

It is believed that EEEH as an antiviral peptide is expressed in response to interferon-mediated gene expression and is a consequence of the innate immune stimulation.

It is reported that RIG-I translocates (moves) along dsRNA at a limited speed, but its movement is significantly accelerated (>20 fold) in the presence of 5'-triphosphate, which is consistent with the viral specific activation of RIG-I (Myong, S. et al., *Science,* 323, 1070, 2009). An in vitro single-molecule fluorescence assay termed PIFE (protein induced fluorescence enhancement) was employed to monitor such movement (Myong, S. et al., *Science,* 323, 1070, 2009). In the presence of Compound 5, RIG-I showed a rapid translocation on dsRNA in a dose-dependent manner, indicating that the compound induced the activation of RIG-I.

For quantitation of RIG-I translocation, Single molecule PIFE yields were estimated. Single molecule PIFE yields are obtained from several hundred molecules simultaneously, allowing statistically reliable data collection. In addition, the data output between the inactive and the active (stimulated) translocation signal was significantly divergent, permitting an accurate discrimination.

The translocation as above was carried out using different concentrations of nucleotide compound. A clear dose-dependence of Compound 5 on RIG-I translocation was observed; increasing the concentration of Compound 5 from 5 μM up to 170 μM resulted in corresponding increase in the proportion of fast translocation.

It is to be noted that Compounds 5 and 6K are each a mixture of two isomers. In the translocation assay, one isomer of Compound 5 designated as Rp 5 isomer [Isomer 1] was more active than the Sp 5 isomer [isomer II]. However, Rp 6K isomer 1 was as active as Sp 6K isomer II. Both Compounds 5 and 6k were strong activators of RIG-I translocation. This result validated the use of translocation assay for assessing the efficacy of Compound 5 in stimulating

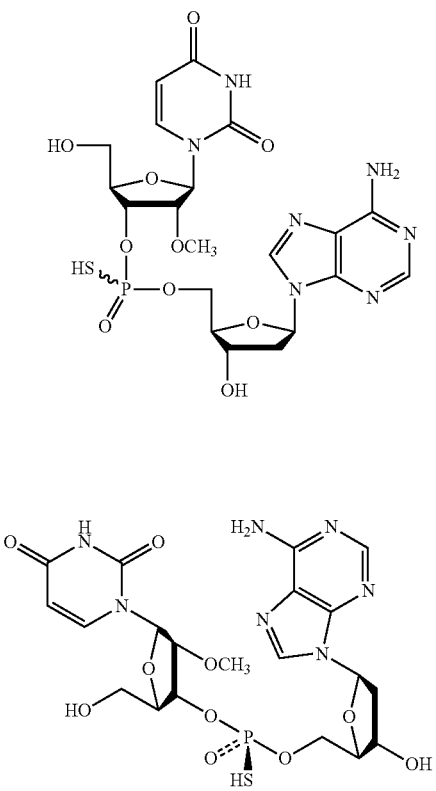
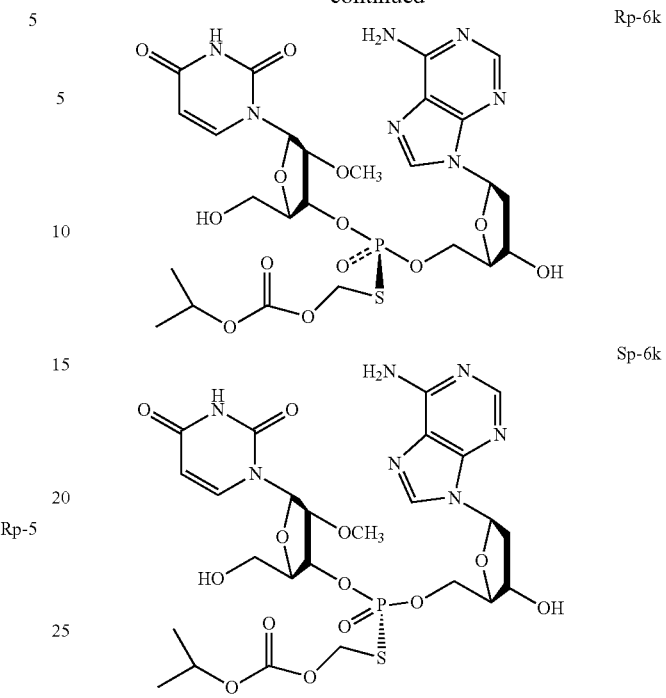
RIG-I activity and was therefore applied to other analogs.
Example 7
Structure-Activity Relationship of RIG-I Translocation
A number of structurally different nucleotide analogs were evaluated in the RIG-I assay (14). The nucleotide analogs SB 50, SB 60, SB 70, SB 80, SB 90, SB 100, and SB 110 show varying degrees of RIG-I translocation on double-stranded RNA.
Moderate RIG-I activators
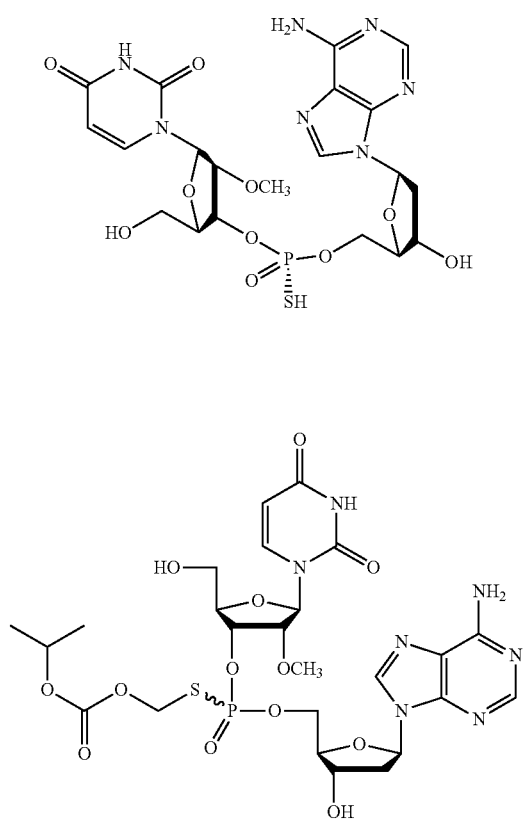
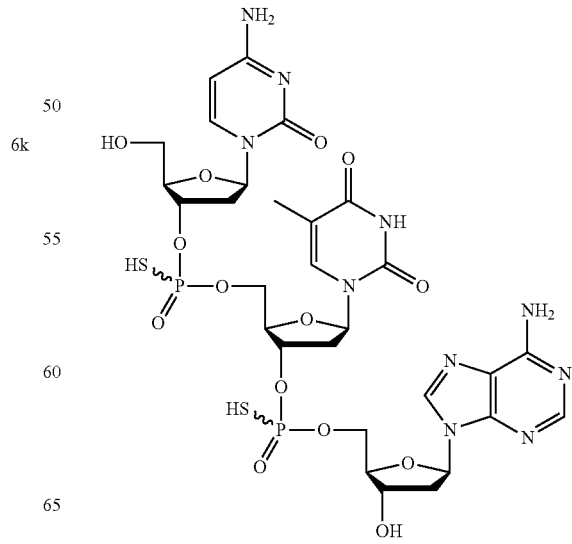

-continued

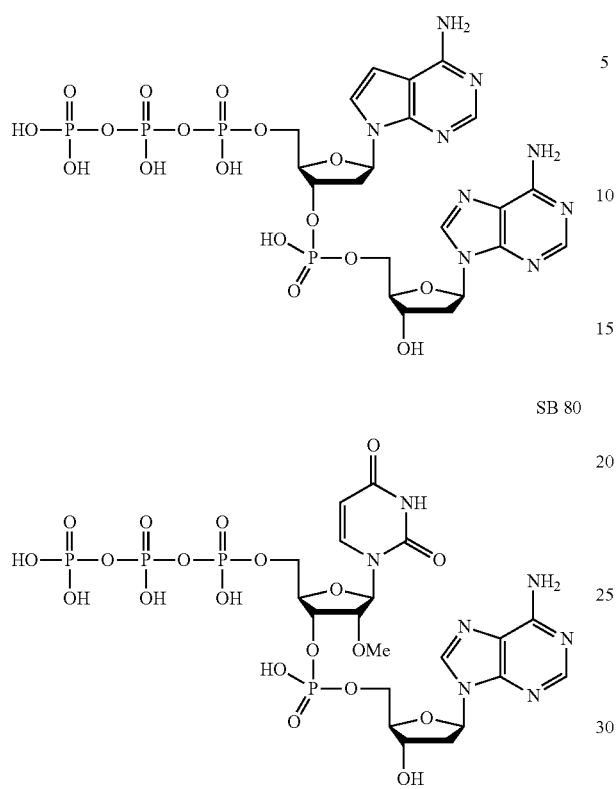

SB 90

SB 80

Weak RIG-I activators

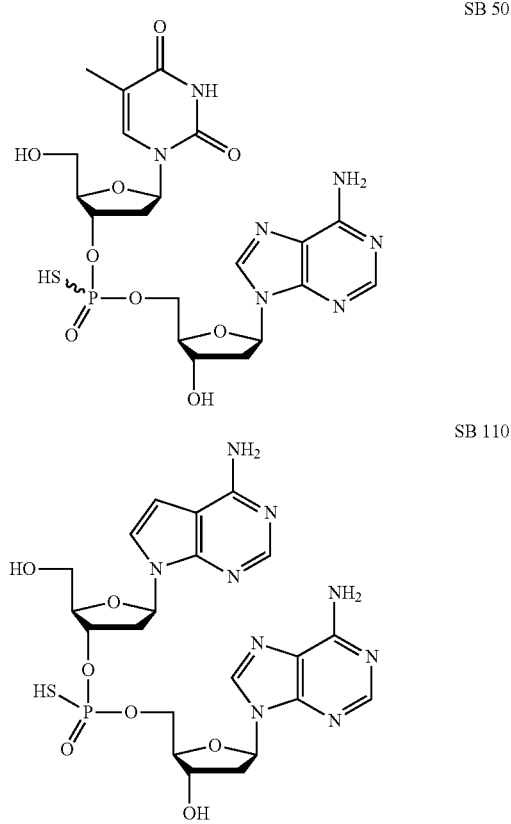

SB 50

SB 110

-continued

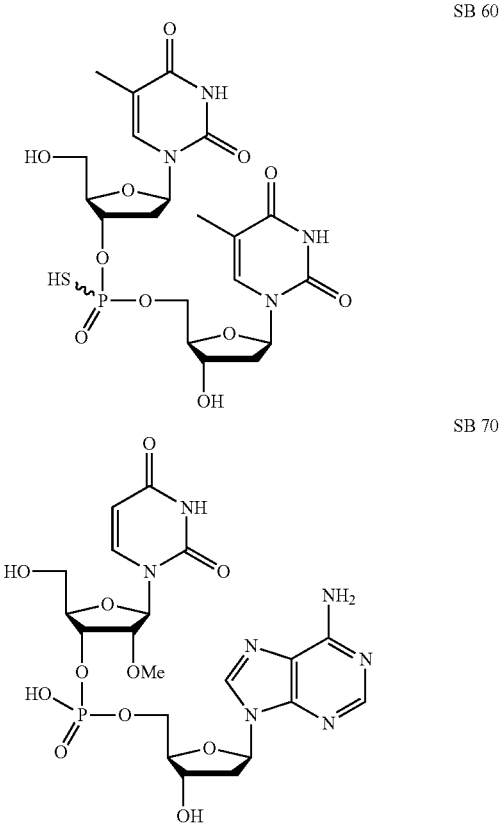

SB 60

SB 70

Example 8

Quantitation of Active vs. Inactive RIG-I Translocation

A standard dsRNA (25 bp) was used as a main substrate for RIG-I translocation assay. The requisite dsRNA substrate with the 3'-Cy3 fluorophore and 5'-biotin was prepared by Dharmacon Inc. Each set of experiment involved multiple rounds of data acquisition from which several hundreds of molecules exhibiting clear translocation behavior was collected. The ratio between rapid (stimulated) translocation and slow translocation would be accounted for in the estimation of compound strength. In order to quantify the affinity of the compound to RIG-I or to RNA substrate, various concentrations of the compound (1-100 μM range) were used in the assay. This enabled the calculation of the association/dissociation constant for each compound, which was a useful measure to apply in cell-based evaluation of compound potency.

The same translocation assay was used on dsRNA, which contains 5'-triphosphate moiety with and without the compound. Test compounds were graded based upon number of molecules translocating and rate of translocation. Rp isomer of Compound 5 (Isomer 1) was the most active of all the analogs tested.

Example 9

Induction of Intracellular IRF3 via Activation of NOD2 by Short Oligonucleotides In the primary assays, di- and trinucleotide compounds were tested for the induction of IRF3 expression in HLE A549 cells, which are known to express NOD2. Compounds 5, SB 43 and 6K, showed 15 to 20 fold infection compared to control untreated cells. The related analogs such as the dinucleotides SB 50, SB 110, and SB 60, induced IRF3 activation to a lesser extent.

Activation of Interferon Regulatory Factor-3 (IRF3)-Luciferase Reporter Gene in Untreated (UT), and HLE A549 Cells Treated with Compounds in the Invention.

HLE cells normally endogenously express NOD2. To determine if short oligonucleotide compounds activate NOD2, HLE cells transfected with IRF3 plasmid were employed. IRF3-luciferase transfected cells were incubated with either DMSO only (UT) or test compounds (1 µM). Following 12 h incubation, Luciferase activity was measured using Dual-Luciferase Reporter Assay System (Promega) according to the manufacturer's protocol. Transfection efficiency was normalized by measuring the expression of renilla Luciferase. Luciferase units (i.e., fold induction) were measured by standard methodology. The assay results are presented as mean±standard deviation (S.D.) from three independent experiments. In general, dinucleotide compounds 3'-dAps-2'-OMeU (5, see also general structure I) and the S-alkylated derivatives SB 43 and 6K caused 15 to 25-fold induction of IRF3.

In other set of experiments, HEK cells that normally do not express NOD2 were transfected with NOD2 and IRG3 and then treated with short oligonucleotide compounds. NOD2 deficient cells failed to induce IRF3 when treated with Compounds 5 and 6K whereas cells that were transfected with NOD2 cause induction of IRF3. Several other compounds showed different degrees of IRF3 activation in NOD-2 transfected cells.

Example 10

Antiviral Activity of Short Oligonucleotide Compounds Against Human Respiratory Syncytial Virus (RSV) Infection (A) RSV infectivity in untreated (UT) and SMNH-treated cells. Human lung epithelial cells were infected with RSV (0.5 MOI) in the absence (DMSO only) or presence of various SMNH compounds (1 µM). At 24 h post-infection, the medium supernatant was collected and the viral titer in the supernatant was assayed by plaque assay analysis using CV-1 cell monolayer. 100% RSV infection represents viral titer from cells incubated with DMSO only (UT cells). The values represent mean±S.D. for three independent determinations. S.D. is shown as error bars.

(B) A typical plaque assay showing RSV infectivity in UT and SMNH-treated cells. Culture supernatant from RSV infected cells (+/−SMNH) was added to CV-1 cells at a dilution of 1×105. Plaques were observed and quantitated on methylcellulose after crystal violet staining.

TABLE 6

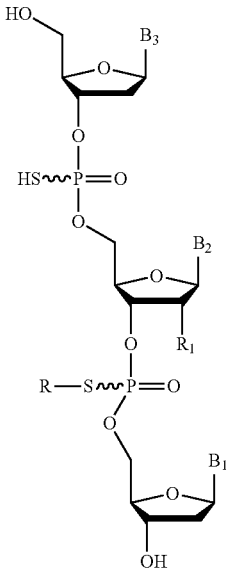

| Compd | $B_1$ | $B_2$ | $B_3$ | R | $R_1$ | Fold induction of IRF3 luciferase activity[#] | % inhibition of RSV at 1 µM |
|---|---|---|---|---|---|---|---|
| 5* | Ade | Ura | — | H | $OCH_3$ | 25 | 82 |
| 6k* | Ade | Ura | — | ![structure] | $OCH_3$ | 22 | n.d. |

TABLE 6-continued

| | | | | | | | |
|---|---|---|---|---|---|---|---|
| 6k-1*@ | Ade | Ura | — | 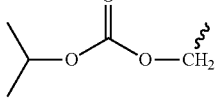 | OCH₃ | 18 | 65 |
| SB 43* | Ade | Ura | — | 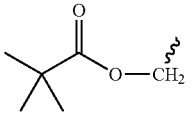 | OCH₃ | 23 | n.d. |
| SB 50* | Ade | Thy | — | H | H | 2 | 0 |
| SB 110* | Ade | 7-deaza | — | H | H | 3 | n.d. |
| SB 60* | Thy | Thy | — | H | H | 3 | n.d. |
| SB 100$ | Ade | Thy | Cyt | H | H | n.d. | 2 |

*dinucleotide;
@$R_p$-isomer of 6k;
$trinucleotide;
in SMNH treated vs. untreated cells;
n.d., not determined Amongst various compounds, the NOD2 activators 5 and 6K elicited maximum antiviral activity causing 60 to 80% suppression of RSV infectivity at 1 μM concentration with other compounds showing varying degrees of antiviral activity (see Table 6).

Example 11

Molecular Modeling Studies

Using molecular modeling, Compounds 5 and 6K was shown to be Adenosine Triphosphate (ATP) mimics. The compounds nicely superimpose on the ATP structure. Thus, Compounds 5 and 6K could bind to nucleotide binding domains in RIG-I and NOD2 that may then cause activation of these proteins that result in induction of IFN pathways.

Example 12

Antiviral Studies Against Hepatitis Viruses in vitro

Selected compounds were evaluated in in vitro cell-based HepG2.2.15 HBV assay. Compounds 5 and 6k were potent anti-HBV compounds, which were found to inhibit intracellular HBV replication of wild type and drug resistant strains in vitro with EC50 in the range of 0.3 to 2 micromolar.

Antiviral Analysis.

For the antiviral analyses, confluent cultures of 2.2.15 cells were maintained on 96-well flat-bottomed tissue culture plates in RPMI1640 medium with 2% fetal bovine serum. Cultures (6 per each test concentration on two replicate plates) were treated with 9 consecutive daily doses of the test compounds. Medium was changed daily with fresh test compounds. HBV nucleic acid and protein levels were measured 24 hours after the last treatment. Extracellular (virion) HBV DNA levels were assessed by quantitative blot hybridization. Intracellular HBV DNA levels were measured by quantitative Southern blot hybridization.

The uptake of neutral red dye was used to determine the relative level of toxicity 24 hours following the last treatment. The absorbance of internalized dye at 510 nM ($A_{510}$) was used for the semi-quantitative analysis. Values are presented as a percentage of the average $A_{510}$ values (±standard deviations) in 9 separate cultures of untreated cells maintained on the 96-well plates seeded at the same time with the identical pool of stock cells used for the antiviral analyses and maintained in an identical manner. A total of 3 cultures were treated with each concentration of the test compound. The antiviral assays were conducted using both wild type and resistant genotypes and the results are summarized in Table 7.

TABLE 7

| | | $EC_{50}$ of 6k (μM) | $EC_{90}$ of 6k (μM) | Control: 3TC (μM) | | Control: ADV (μM) | |
|---|---|---|---|---|---|---|---|
| Virus | Strain | | | $EC_{50}$ | $EC_{90}$ | $EC_{50}$ | $EC_{90}$ |
| HBV | WT | 2.5 | 8.5 | 0.2 | 0.7 | 1.5 | 7 |
| HBV-3TC-R1 | L180M | 2.1 | 8.6 | 5.3 | 20 | 2.1 | 8.2 |
| HBV-3TC-R2 | M204V | 2.4 | 8.3 | >100 | >100 | 1.8 | 7.2 |
| HBV-3TC-R3 | M204I | 3 | 9.2 | >100 | >100 | 2 | 8 |
| HBV-3TC-R4 | LMMV | 3.1 | 9.3 | >100 | >100 | 2.2 | 8.3 |
| HBV-ADV-R1 | N236T | 2.8 | 8.7 | 0.2 | 0.8 | 7.5 | 29 |

Example 13

In vivo Antiviral Studies (a) Effect of i.p. Administration of Compound 5 on Hepatitis B Virus in Transgenic Mice.

Compound 5 was evaluated in transgenic mice expressing hepatitis B virus (HBV). Compound 5 was administered intraperitoneally once daily for 14 days at a dosage of 100 mg/kg/day, in either saline or cremaphor: ethanol:saline vehicles, significantly reduced liver HBV DNA (P≤0.001). Its activity was also similar to the adefovir dipivoxil (ADV) anti-HBV activity; however, the two compounds seemed to suppress different HBV DNA species. ADV did not remove very low-sized viral bands on the Southern blot analysis and preferentially removed the higher sized bands. In contrast, Compound 5 appeared to indiscriminately remove all HBV DNA species, including the bands typically left by ADV, which may reflect a different mechanism of action other than classical chain termination. Serum HBe, liver HBs, and HBc were not affected by Compound 5 treatment, which is consistent in transgenic mice with compounds that block viral synthesis "downstream" from mRNA synthesis, such as blockage of polymerase activities. A minimal effective dosage was determined to be between 1.6-0.5 mg/kg/day, which was similar to ADV minimal effective dosage of 1.0 mg/kg/day (Table 8). Table 8 shows effect of Compound 5 on HBV DNA in male transgenic mice treated intraperitoneally once daily for 14 days.

>100 micromolar. Recombinant human interferon 2b (PBL laboratories, Inc.) is used as an assay control. Compound 6k had $EC_{50}$ between 1 and 2 micromolar; Sp6k had $EC_{50}$ of 0.3 µM; Compound 5 had $EC_{50}$ of about 3 µM; Rp5 had $EC_{50}$ of 0.16 µM, b. Secondary Anti-HCV Assay This assay assesses activity against additional genotypes using the format described for the primary assay. Activity against the genotype 1b HCV was included for comparison. A replicon cell line containing H/FL-Neo (genotype 1a (H77), full length construct) (Blight, et al., 2003, J. Virol. 77:3181) was used. Compound 6K had an $EC_{50}$ of 1 micromolar and $EC_{90}$ of about 6 micromolar.

TABLE 8

| Compound | Dosage (mg/kg/d) | Weight gain (g ± stdev) | Liver HBV DNA (mean pg viral/µg cellular DNA ± stdev) (n)[a] | Liver HBV RNA (mean relative units ± stdev) | Liver HBcAg (mean stained cells/100 X field ± stdev) | Serum HBV DNA (mean $log_{10}$ genome equivalents/mL serum ± stdev) (n) | Serum HBeAg (mean ng/mL ± stdev) | Serum HBsAg (mean ng/mL ± stdev) |
|---|---|---|---|---|---|---|---|---|
| 5 | 100 | 1.0 ± 0.6 | 1.7 ± 1.5 (9)*** | 1.7 ± 0.3 | 24 ± 15 | 5.4 ± 0.6 (7) | 1241 ± 279 | 28 ± 15 |
| ADV[b] | 10 | 0.9 ± 0.7 | 2.7 ± 1.4 (9)*** | — | — | 4.9 ± 0.4 (9) | — | — |
| C:E:S vehicle[c] | — | 1.5 ± 0.7 | 18.3 ± 20.8 (10) | 1.6 ± 0.4 | 16 ± 9 | 5.4 ± 0.2 (10) | 1311 ± 284 | 46 ± 31 |
| 5 | 100 | 0.4 ± 0.8 | 0.3 ± 0.4 (8)*** | — | — | 5.0 ± 0.3 (8) | — | — |
| saline placebo | — | 0.6 ± 1.3 | 6.9 ± 3.3 (5) | — | — | 5.9 ± 1.2 (6) | — | — |

[a]Number of samples. Any difference between number of samples and alive/total is because some sample preparation may have been incomplete or undesirable to properly finish the analysis.
[b]adefovir dipivoxil
[c]cremaphor:ethanol:saline (10:10:30)
***P < 0.001 compared with vehicle placebo
**P < 0.05 compared with vehicle placebo
*P < 0.01 compared with vehicle placebo Example 14

Antiviral Activity of Compound 6K Against Hepatitis C Virus a. Primary Anti-HCV Assay Antiviral activity against HCV was assessed in a 3-day assay (Okuse, et al., 2005; Antiviral. Res. 65:23; Korba, et al., 2008, Antiviral Res. 77:56) using the stably-expressing HCV replicon cell line, AVA5 (sub-genomic (CONI), genotype 1b) (Blight, et al., 2000, Science 290:1972) maintained as sub-confluent cultures on 96-well plates. Antiviral activity was determined by blot hybridization analysis of intracellular HCV RNA (normalized to the level of cellular B-actin RNA in each culture sample). Cytotoxicity was assessed by neutral red dye uptake in cultures maintained in parallel plates.

$EC_{50}$, $EC_{90}$, and $CC_{50}$ values were calculated by linear regression analysis (MS EXCEL®, QuattroPro®) using data combined from all treated cultures Korba & Gerin, 1992, Antivir. Res. 19:55; Okuse, et al., 2005, Antivir. Res. 65:23). Standard deviations for $EC_{50}$ and $EC_{90}$ values are calculated from the standard errors generated by the regression analyses. $EC_{50}$ and $EC_{90}$ are drug concentrations at which a 2-fold, or a 10-fold depression of intracellular HCV RNA (relative to the average levels in untreated cultures), respectively was observed. Compound 6K had an $EC_{50}$ of 2 micromolar and $EC_{90}$ of about 8 micromolar. $CC_{50}$, the drug concentration at which a 2-fold lower level of neutral red dye uptake (relative to the average levels in untreated cultures) is observed was Example 15

Synergistic Activity of Compound 6k Against HCV when Combined with Other Antivirals In order to demonstrate that leads can be synergistically combined with other antivirals, combination studies with known anti-HCV polymerase and protease inhibitors, as well as, ribavirin and interferon, are performed.

Combination treatments are conducted as previously described. Briefly, two agents were mixed together at a predetermined concentration ratio. The relative ratios of the individual agents were based on the monotherapy values of each compound (drug concentrations at which a 10-fold reduction of HCV RNA is observed [$EC_{90}$s]). For each combination of agents, three concentration ratios, centered upon the use of the compounds at equipotent antiviral concentrations, were used. A dilution series (six three-fold-concentration steps, beginning at the approximate $EC_{90}$s) was then generated with the concentration ratio of the two agents remaining the same in each dilution step. Separate dilution series of monotherapy with each individual antiviral agent at the same concentrations was also used to treat cultures in the same experiment. Toxicity analysis was performed as described above for the monotherapies. Analysis of drug interactions in the combination studies was determined by the use of the CALCUSYN program (Biosoft, Inc., Cambridge, United Kingdom). This program evaluates synergy, additivity, or antagonism by use of several methodologies, including that of Chou and Talalay with a statistical analysis employing the Monte Carlo technique to provide confidence limits, fraction-affected-confidence interval (FA-CI) plots, isobolograms, and median-effect plots [Belenkii, M. S. Schinazi, R. A method for the analysis of combination therapies with statistical analysis. *Antiviral Res.* 25, 11, 2005].

Compound 6k was active against HCV genotype 1b ($EC_{50}$ about 1 to 2 micromolar) and showed synergistic activity when combined with other classes of anti-HCV drugs in replicon assays. The results are summarized FIG. 9.

Several other compounds also showed varying degrees of antiviral activity in the replicon assays.

It is pertinent to mention that nucleotide compounds, in addition to interferon stimulating activity, could also directly act on other viral targets as inhibitors of viral replication thereby providing multiple mechanisms of antiviral action. Therefore, these compounds can be expected to be synergistic with other antivirals and can be used in combination therapy with a potential for eradication of the virus. These compounds are also expected to have broad-spectrum antiviral activity against multiple viral genotypes and resistant strains. Since these compounds have immunostimulatory potential, they can also be used potentially as prophylactic and/or adjuvants with vaccines.

Example 16

Antiviral Activity of Compounds Against Influenza Virus

To evaluate whether the compounds inhibit the in vitro and in vivo replication of influenza viruses, the mouse-adapted H1N1 influenza A/WSN/33 and A/PR8/34 viruses is used. For in vitro studies, cells are treated with varying (0.5-10 μM) concentrations of the compounds and the ability of these cells in inhibiting influenza virus replication is ascertained in single-cycle and multicycle replication studies by determining the HA and pfu titers at various time points postinfection. Cell toxicity is monitored via CellTiter 96 Cell Proliferation Assays (Promega), with the results used to calculate $IC_{50}$ (inhibitory concentration resulting in 50% inhibition of viral replication) values. To serve as a positive control of inhibition and for comparative purposes, the FDA-approved neuraminidase inhibitor oseltamivir is used.

To investigate the antiviral activities of the compounds in vivo, a mouse model of influenza virus infection is used. The intranasal infection of Balb/c mice with the influenza PR8 virus results in severe pneumonia with an $LD_{50}$ of $10^3$ pfu and a time of death of around 7-8 days postinfection, at which point the infected mouse will have lost more than 25% of its body weight and the histopathology of its lungs revealing the destruction of lung architecture, high levels of neutrophilic, monocytic, and lymphocytic infiltrations, and the loss of epithelial cells lining the bronchi. Pilot experiments are conducted in mice to estimate the MED (minimal effective dose) and MTD (minimal tolerable dose) of the lead compounds. For example, the $EC_{50}$ of Compound 6k is approximately 10 mg/kg when administered orally to a hepatitis B transgenic mouse model. For the purposes to estimate the MTD of the compounds, groups of five mice a piece are administered daily with various concentrations of the lead compounds intranasally for five days, with tolerability monitored by the measurement of body weights for one week, after which the mice will be sacrificed and histopathological slides of their lungs prepared to examine for any signs of damage. Once the MED and MTD are determined, groups of 19 mice are intranasally infected with 10 $LD_{50}$ of the PR8 virus and intranasally treated daily with the compounds. Three mice are sacrificed at days 2, 4, and 6 to determine viral titers and histopathology performed on their lungs (one lung is used for viral titers and the other for histopathology for each mouse). The remaining 10 mice are used to monitor survival. Any loss of body weight is monitored as an indicator of disease, with the mice euthanized and recorded as dead if body weight loss ever exceeds 20%, in accordance with existing IACUC recommendations. Non-treated mice and mice treated with oseltamivir serves as the controls. To confirm the specificity of the action of the compounds in RIG-I signaling activity, RIG-I−/−mice is included in the in vivo infection studies. Wild type mice but not RIG-I−/−mice treated with compound exhibit increased survival and decreases in viral titers, lung immunopathology, and sero-conversion. In protection experiments designed to evaluate protection from infection, the mice are treated with the compounds at days 1, 2 and 3 post-exposure to the influenza PR8 virus.

Example 17

In vitro Cytotoxicity Studies of the Compounds Using a Panel of Cell Lines Predictive of Liver, Kidney, Bone Marrow and Mitochondrial Toxicity Compounds 5 and 6k have excellent safety profile with $CC_{50}$>1000 micromolar in a number of cell lines. Standard MTT assays were performed in 96-well plates using the Promega CellTiter96 Non-radioactive Cell Proliferation Assay Kit in conjunction with a 96-well Plate Reader (ThermoMax, Molecular devices), and MDBK, Vero, and HFF cell lines (obtained from ATCC). Several controls were employed including the nucleoside analogs 3TC, AZT, and ddC, as well as, media without drugs. SDS was used as a positive cytotoxic control. The compounds were tested in triplicate at concentrations of 100, 300, and 1000 μM. Following a 24-hour incubation of cells with the test substance, the MTT assay was carried out. All tested compounds showed CC50>1000 micromolar indicating high safety index for the compounds.

Example 18

Induction of Interferon in PBMCs Treated with the BCG and Compounds

Figure 6:
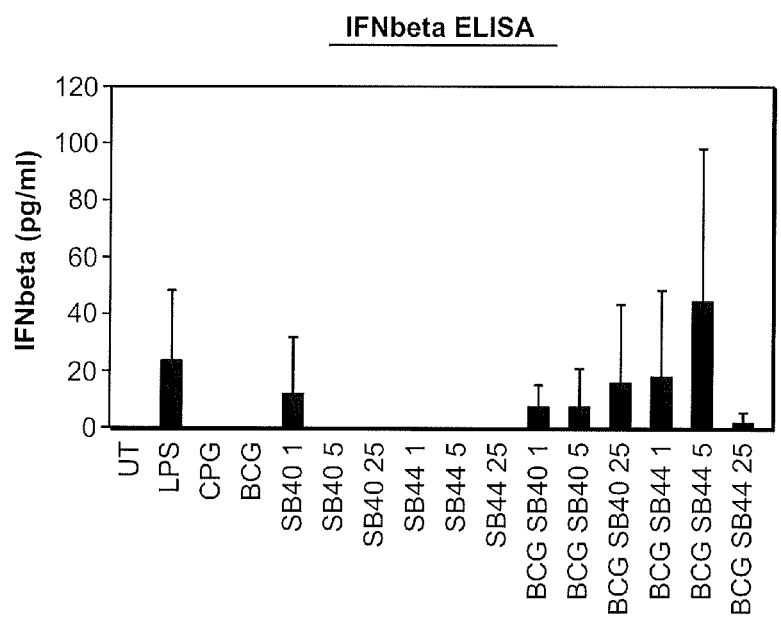
FIG. 6 is a micrograph showing induction of IFN beta in PBMCs treated with Compounds 5 and 6k in the presence of BCG effect on Interleukin-2 production by macrophages.

For this assay, PBMCs were plated at 1 million cells per ml in 24 well plates. Groups of plates were treated with BCG, BCG+compounds, and incubated for 24 hrs. The cells were lysed and the supernatants harvested. The production of cytokines and type I Interferon was assessed using the ELISA assay with standard kits. BCG did induce other cytokines (IL-1, 6, 8, 10 and TNF) from the same exp. Cells treated with BCG and compounds induced increased production of IFN compared to BCG alone. The results are shown in FIG. 6.

Example 19

Effect of Compounds 5 and 6k on Interleukin-2 Production by Macrophages

Figure 7:
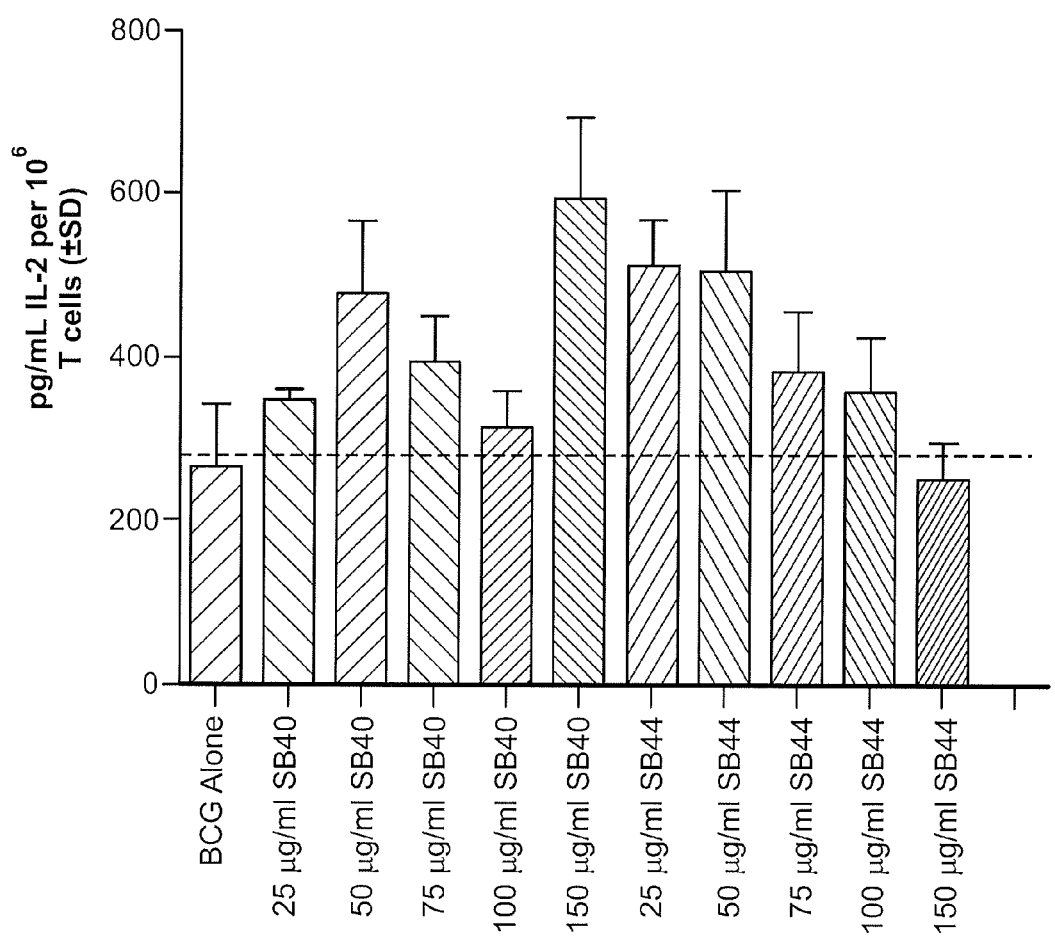
FIG. 7 depicts effects on IL2 expression in BCG-primed macrophages by oligonucleotide analogs (Compound 5 is shown as SB 40, and Compound 6k is shown as SB 44).

To ascertain that the compounds induced Interleukin 2 production, macrophages were treated with the compounds along with BCG. Control cells used were untreated cells, and those treated with BCG. Following incubation for 18 hrs, the macrophages were overlaid with T cells and IL-2 levels were quantitated. Compounds 5 and 6k showed induction of IL-2 in those cells that also received BCG compared to BCG alone (see FIG. 7).

In summary, the compounds of the invention act as activators of intracellular microbial sensors and cause activation of immune response. The compounds also showed antiviral activity against DNA virus (HBV) and RNA viruses such as HCV and RSV. The claimed compounds can be used not only to induce immune response as agonists and can also be used to block (antagonize) undesired immune response in autoimmune diseases. Hence these compounds can also be used in a variety of therapeutic settings including but limited to cancer and autoimmune diseases.

We claim:

1. A method of measuring an antimicrobial response in a subject in need thereof and suffering from an microbial infection, said method comprising measuring an expression level of cellular EEEH protein as a biomarker.

* * * * *